United States Patent
Karunanandaa et al.

(10) Patent No.: US 7,105,730 B1
(45) Date of Patent: Sep. 12, 2006

(54) NUCLEIC ACID MOLECULES AND OTHER MOLECULES ASSOCIATED WITH STEROL SYNTHESIS AND METABOLISM

(75) Inventors: Balasulojini Karunanandaa, Creve Coeur, MO (US); Jaehyuk Yu, Madison, WI (US); Ganesh M. Kishore, Creve Coeur, MO (US)

(73) Assignee: Monsanto Technology L.L.C., St. Louis, MO (US)

( * ) Notice: Subject to any disclaimer, the term of this patent is extended or adjusted under 35 U.S.C. 154(b) by 353 days.

(21) Appl. No.: 10/030,537

(22) PCT Filed: Jul. 11, 2000

(86) PCT No.: PCT/US00/18813

§ 371 (c)(1),
(2), (4) Date: Apr. 23, 2002

(87) PCT Pub. No.: WO01/04314

PCT Pub. Date: Jan. 18, 2001

Related U.S. Application Data

(60) Provisional application No. 60/142,981, filed on Jul. 12, 1999.

(51) Int. Cl.
C12N 15/29 (2006.01)
C12N 15/82 (2006.01)
A01H 5/00 (2006.01)

(52) U.S. Cl. .................. 800/320.1; 800/298; 800/306; 800/312; 536/23.1; 536/23.6

(58) Field of Classification Search ................ 800/278, 800/281, 288, 298, 306, 312, 313, 314, 320.1, 800/322; 536/23.1, 23.2, 23.6, 23.7, 23.74
See application file for complete search history.

(56) References Cited

OTHER PUBLICATIONS

Jiang B. et al., Yeast, 1994, vol. 10, pp. 341-353.*
Doerks et al., TIG, 14: 248-250 1998.*
Smith et al. Nature Biotechnology 15:1222-1223, Nov. 1997.*
Brenner TIG 15, 4:132-133, Apr. 1999.*
Bork et al. TIG 12, 10:425-427, Oct. 1996.*
Venter C. et al., Science, 2001; vol. 291, pp. 1304-1351.*
Fang M. et al. The EMBO Journal ; vol. 15, No. 23; pp. 6447-6459.*
Broun et al. Science, vol. 282, Nov. 13, 1998; pp. 1315-1317.*
Casper, Steven J., et al., Expression of the Green Fluorescent Protein-Encoding Gene from a Tobacco Mosaic Virus-Based Vector, *Gene*, 173:69-73 (1996).

Crowley, James H., et al., A Mutation in a Purported Regulatory Gene Affects Control of Sterol Uptake in *Saccharomyces cerevisiae*, *Journal of Bacteriology*, 180(16):4177-4183 (Aug. 1998).
Fang, Min, et al., Keslp Shares Homology with Human Oxysterol Binding Protein and Participates in a Novel Regulatory Pathway for Yeast Golgi-Derived Transport Vesicle Biogenesis, *The EMBO Journal*, 15(23):6447-6459 (Dec. 1996).
International Search Report, PCT/US00/18813, pp. 1-2 (May 2000).
Jiang, Bo, et al., A New Family of Yeast Genes Implicated in Ergosterol Synthesis is Related to the Human Oxysterol Binding Protein, *Yeast*, 10(3):341-353 (Mar. 1994).
Kaneko, Takakazu, et al., Structural Analysis of *Arabidopsis thaliana* Chromosome 5. IX. Sequence Features of the Regions of 1,011,550 bp Covered by Seventeen P1 and TAC Clones, *DNA Research* 6(3):183-195 (1999).
Lyne, M., et al., *SWALL* Accession No.: 074178 (Nov. 1998).
Nakamura, Y., *EMBL* Accession No. AB025604 (Dec. 2000).
Newman, Tom, et al., Genes Galore: A Summary of Methods for Accessing Results from Large-Scale Partial Sequencing of Anonymous *Arabidopsis* cDNA Clones, *Plant Physiology*, 106(4):1241-1255 (Dec. 1994).
Shoemaker, R., et al., *EMBL* Accession No. AW596698 (Mar. 2000).
Hynynen, Riikka et al., "Overexpression of OSBP-Related Protein 2 (ORP2) Induces Changes in Cellular Cho9lesterol Metabolism and Enhances Endocytosis", *Biochem. J.*, vol. 390, (2005), pp. 273-283.
Im, Young Jun et al., "Structural Mechanism for Sterol Sensing and Transport by OSBP-Related Proteins", *Nature*, vol. 437, Sep. 1, 2005, pp. 154-158.
Levine, Tim, "A New Way for Sterols to Walk on Water", *Molecular Cell*, Vo. 19, Sep. 16, 2005, pp. 722-723.

* cited by examiner

*Primary Examiner*—Russell P. Kallis
(74) *Attorney, Agent, or Firm*—Chunping Li; Arnold & Porter LLP

(57) ABSTRACT

This invention relates to the field of biotechnology, particularly as it pertains to the production of sterols in a variety of host systems particularly plants. More specifically, the invention relates to nucleic acid molecules encoding proteins and fragments of proteins associated with sterol and phytosterol metabolism as well as the encoded proteins and fragments of proteins and antibodies capable of binding to them. The invention also relates to methods of using the nucleic acid molecules, fragments of the nucleic acid molecules, proteins, and fragments of proteins. The invention also relates to cells, organisms, particularly plants, or seeds, or progeny of plants, that have been manipulated to contain increased levels or overexpress at least one sterol or phytosterol compound.

8 Claims, No Drawings

NUCLEIC ACID MOLECULES AND OTHER MOLECULES ASSOCIATED WITH STEROL SYNTHESIS AND METABOLISM

CROSS-REFERENCE TO RELATED APPLICATIONS

This application is the National Stage of International Application No. PCT/US00/18813, filed 11 Jul. 2000. This application claims the benefit of U.S. Provisional Application No. 60/142,981, filed on 12 Jul. 1999.

INCORPORATION OF SEQUENCE LISTING

A paper copy of the Sequence Listing and a computer readable form of the sequence listing on diskette, containing the file named SeqList.txt, which is 55,428 bytes in size (measured in MS-DOS), and which was created on Jan. 10, 2002, are herein incorporated by reference.

FIELD OF THE INVENTION

This invention relates to the field of biotechnology, particularly as it pertains to the production of sterols in a variety of host systems particularly plants. More specifically, the invention relates to nucleic acid molecules encoding proteins and fragments of proteins associated with sterol and phytosterol metabolism as well as the encoded proteins and fragments of proteins and antibodies capable of binding to them. The invention also relates to methods of using the nucleic acid molecules, fragments of the nucleic acid molecules, proteins, and fragments of proteins. The invention also relates to cells, organisms, particularly plants, or seeds, or progeny of plants, that have been manipulated to contain increased levels or overexpress at least one sterol or phytosterol compound.

BACKGROUND OF THE INVENTION

Sterols are a class of essential, natural compounds required by all eukaryotes to complete their life cycle. The types of sterols produced and predominantly present within each of the phylogenetic kingdoms varies. Plants produce a class of sterols called phytosterols. A phytosterol called sitosterol predominates. In animals, cholesterol is typically the major sterol while in fungi it is ergosterol.

Phytosterols from plants possess a wide spectrum of biological activities in animals and humans. Phytosterols are considered efficacious cholesterol-lowering agents (Pelletier et al., *Annals Nutrit. Metab.* 39:291–295 (1995), the entirety of which is herein incorporated by reference). Lower cholesterol levels are linked to a reduction in the risk to cardiovascular disease. Phytosterols can also block cholesterol absorption in the intestine, which would also lead to lower cholesterol levels. Thus, enhancing the levels of phytosterols in edible plants and seeds, or products derived from these plants and seeds, may lead to food products with increased nutritive or therapeutic value.

In one aspect, this invention provides these desirable plants and seeds as well as methods to produce them. Since, as will be discussed below, the genetic manipulation made possible by this invention involves families of related genes that cross phylogenetic boundaries, the effects are not limited to plants alone.

Biochemistry of Sterol Synthesis

A number of the important sterol biosynthetic enzymes, reactions, and intermediates have been described. Sterol synthesis uses acetyl CoA as the basic carbon building block. Multiple acetyl CoA molecules form the five-carbon isoprene units, hence the name isoprenoid pathway. Enzymatic combination of isoprene units leads to the thirty-carbon squalene molecule, which is the penultimate precursor to sterols.

Throughout plants, animals, and fungus, the reactions proceed as: acetyl CoA_HMGCoA, mevalonate, mevalonate 5 phosphate, mevalonate 5-pyrophosphate, isopentyl diphosphate, 5-pyrophosphatemevalonate, isopentyl pyrophosphate (PIP), dimethylallyl pyrophosphate (DMAPP), PIP+DMAPP, geranyl pyrophosphate+IPP, farnesyl pyrophosphate, 2 farnesyl pyrophosphate, squalene and squalene epoxide From squalene epoxide, the sterol biosynthesis pathway of plants diverges from that of animals and fungi. In plants, cycloartenol is produced next by cyclization of squalene epoxide. The plant pathway eventually leads to the synthesis of the predominant phytosterol, sitosterol.

Animals go on to produce lanosterol from squalene epoxide, eventually leading to cholesterol, which is the precursor to steroid hormones and bile acids, among other compounds. In fungi, lanosterol leads to the production of the predominant sterol, ergosterol.

An important regulatory control step within the pathway consists of the HMGCoA_Mevalonate step, catalyzed by HMGCoA reductase, and the condensation of 2 farnesyl pyrophosphates_squalene, catalyzed by squalene synthase. An early, reported rate-limiting step, in the pathway is the HMGCoA reductase-catalyzed reaction.

A number of studies have focused on the regulation of HMGCoA reductase. HMGCoA reductase (EC 1.1.1.34) catalyzes the reductive conversion of HMGCoA to mevalonic acid (MVA). This reaction is the controlling step in isoprenoid biosynthesis. The enzyme is regulated by feedback mechanisms and by a system of activation kinases and phosphatases (Gray, *Adv. Bot. Res.*, 14: 25 (1987); Bach et al., *Lipids*, 26: 637 (1991); Stermer et al., *J. Lipid Res.*, 35: 1133 (1994), all of which are herein incorporated by reference in their entirety).

Another important regulation occurs at the squalene synthase step. Squalene synthase (EC 2.5.1.21) reductively condenses two molecules of FPP in the presence of $Mg^{2+}$ and NADPH to form squalene. The reaction involves a head-to-head condensation and forms a stable intermediate, presqualene diphosphate. The enzyme is subject to regulation similar to that of HMGCoA reductase and acts by balancing the incorporation of FPP into sterols and other compounds.

The sterol pathway of plants diverges from that in animals and fungi after squalene epoxide. In plants, the cyclization of squalene epoxide occurs next, under the regulated control of cycloartenol synthase (EC 5.4.99.8). The cyclization mechanism proceeds from the epoxy end into a chair-boat-chair-boat sequence that is mediated by a transient C-20 carbocationic intermediate. The reported rate-limiting step in plant sterol synthesis occurs in the next step, S-adenosyl-L-methionine:sterol C-24 methyl transferase (EC 2.1.1.41) ($SMT_I$) catalyzing the transfer of a methyl group from a cofactor, S-adenosyl-L-methionine, to the C-24 center of the sterol side chain. This is the first of two methyl transfer reactions. The second methyl transfer reaction occurs further down in the pathway and has been reported to be catalyzed by $SMT_{II}$. An isoform enzyme, $SMT_{II}$, catalyzes the conversion of 24-methylene lophenol to 24-ethylidene lophenol (Fonteneau et al., *Plant Sci Lett* 10: 147–155(1977), the entirety of which is herein incorporated by reference). The presence of two distinct SMTs in plants were further confirmed by cloning cDNAs code the enzymes from *Arabidopsis* (Husselstein et al., *FEBS Lett* 381:87–92(1996), the entirety of which is herein incorporated by reference), soybean (Shi et al., *J Biol Chem* 271: 9384–9389(1996), the entirety of which is herein incorporated by reference), maize (Grebenok et al., *Plant Mol Biol* 34: 891–896(1997), the entirety of which is herein incorporated by reference) and tobacco (Bouvier-Nave et al., *Eur J Biochem* 246: 518–529 (1997); Bouvier-Nave et al., *Eur J Biochem* 256: 88–96 (1998), both of which are herein incorporated by reference in their entirety).

Later in the pathway, a sterol C-14 demethylase catalyzes the demethylation at C-14, removing the methyl group and creating a double bond. Interestingly, this enzyme also occurs in plants and fungi, but at a different point in the pathway. Sterol C14-demethylation is mediated by a cytochrome P-450 complex. A large family of enzymes utilize the cytochrome P-450 complex. There is, in addition, a family of cytochrome P450 complexes. Sterol C-22 desaturase (EC 2.7.3.9) catalyzes the formation of the double bond at C-22 on the side chain. The C-22 desaturase in yeast, which is the final step in the biosynthesis of ergosterol, contains a cytochrome P450 that is distinct from the cytochrome P450 participating in the demethylation reaction. Additional cytochrome P450 enzymes participate in brassinosteroid synthesis (Bishop, *Plant Cell* 8:959–969 (1996), the entirety of which is herein incorporated by reference). Brassinosteroids are steroidal compounds with plant growth regulatory properties, including modulation of cell expansion and photomorphogenesis (Artecal, *Plant Hormones, Physiology, Biochemistry and Molecular Biology* ed. Davies, Kluwer Academic Publishers, Dordrecht, 66 (1995), Yakota, *Trends in Plant Science* 2:137–143 (1997), both of which are herein incorporated by reference in their entirety).

One class of proteins, oxysterol-binding proteins, have been reported in humans and yeast (Jiang et al., *Yeast* 10:341–353 (1994), the entirety of which is herein incorporated by reference). These proteins have been reported to modulate ergosterol levels in yeast (Jiang et al., *Yeast* 10: 341–353 (1994)). In particular, Jiang et al., reported three genes KES1, HES1 and OSH1, which encode proteins containing an oxysterol-binding region.

The present invention provides a gene, hes1, involved in plant phytosterol production. Expression of HES1 (protein) in organisms, such as plants, can increase phytosterol biosynthesis. The present invention also provides transgenic organisms expressing a HES1 protein, which can enhance food and feed sources.

SUMMARY OF THE INVENTION

The present invention includes a substantially purified nucleic acid molecule that encodes a protein comprising the amino acid sequence of SEQ ID NO: 30.

The present invention includes a substantially purified nucleic acid molecule that specifically hybridizes to a nucleic acid sequence of SEQ ID NO: 1 or its complement, wherein the nucleic acid molecule encodes a protein comprising the amino acid sequence of SEQ ID NO: 30.

The present invention includes a substantially purified nucleic acid molecule that encodes a protein comprising the amino acid sequence of SEQ ID NO: 31.

The present invention includes a substantially purified nucleic acid molecule that specifically hybridizes to a nucleic acid sequence of SEQ ID NO: 2 or its complement, wherein the nucleic acid molecule encodes a protein comprising the amino acid sequence of SEQ ID NO: 31.

The present invention includes a substantially purified nucleic acid molecule that encodes a protein comprising the amino acid sequence of SEQ ID NO: 32.

The present invention includes a substantially purified nucleic acid molecule that specifically hybridizes to a nucleic acid sequence of SEQ ID NO: 3 or its complement, wherein the nucleic acid molecule encodes a protein comprising the amino acid sequence of SEQ ID NO: 32.

The present invention includes a substantially purified nucleic acid molecule that encodes a protein comprising the amino acid sequence of SEQ ID NO: 33.

The present invention includes a substantially purified nucleic acid molecule that specifically hybridizes to a nucleic acid sequence of SEQ ID NO: 4 or its complement, wherein the nucleic acid molecule encodes a protein comprising the amino acid sequence of SEQ ID NO: 33.

The present invention includes a substantially purified nucleic acid molecule comprising a nucleic acid sequence which encodes a plant HES1 protein.

The present invention includes an antibody capable of specifically binding a protein comprising the amino acid sequence of SEQ ID NO: 30.

The present invention includes an antibody capable of specifically binding a protein comprising the amino acid sequence of SEQ ID NO: 31.

The present invention includes an antibody capable of specifically binding a protein comprising the amino acid sequence of SEQ ID NO: 32.

The present invention includes an antibody capable of specifically binding a protein comprising the amino acid sequence of SEQ ID NO: 33.

The present invention includes a plant having a nucleic acid molecule which comprises: (A) a promoter region which functions in a plant cell to cause the production of a mRNA molecule; (B) an exogenous structural nucleic acid molecule encoding a protein or fragment thereof comprising an amino acid sequence selected from the group consisting of SEQ ID NOs: 30, 31, 32, 33 and 34, and (C) a 3' non-translated sequence that functions in the plant cell to cause termination of transcription and addition of polyadenylated ribonucleotides to a 3' end of the mRNA molecule.

The present invention includes a transformed plant having a nucleic acid molecule which comprises: (A) an exogenous promoter region which functions in a plant cell to cause the production of a mRNA molecule; which is linked to (B) a transcribed nucleic acid molecule with a transcribed strand and a non-transcribed strand, wherein the transcribed strand is complementary to a nucleic acid molecule encoding a protein comprising an amino acid sequence selected from the group consisting of SEQ ID NOs: 30, 31, 32, 33, and 34, which is linked to (C) a 3' non-translated sequence that functions in plant cells to cause termination of transcription and addition of polyadenylated ribonucleotides to a 3' end of the mRNA molecule.

The present invention includes a plant having a nucleic acid molecule which comprises: (A) a promoter region which functions in a plant cell to cause the production of a mRNA molecule; (1) an exogenous structural nucleic acid molecule encoding a plant HES1 protein or fragment thereof, and (C) a 3' non-translated sequence that functions in the plant cell to cause termination of transcription and addition of polyadenylated ribonucleotides to a 3' end of the mRNA molecule.

The present invention includes a plant having a nucleic acid molecule which comprises: (A) a promoter region which functions in a plant cell to cause the production of a mRNA molecule; (B) an exogenous structural nucleic acid molecule encoding a HES1 protein or fragment thereof, and (C) a 3' non-translated sequence that functions in the plant cell to cause termination of transcription and addition of polyadenylated ribonucleotides to a 3' end of the mRNA molecule.

The present invention includes and provides a method of producing a plant containing an expressed HES1 protein or fragment thereof in a plant comprising: (A) transforming the plant with a functional nucleic acid molecule, wherein the functional nucleic acid molecule comprises a promoter region, wherein the promoter region is linked to a structural region, wherein the structural region comprises a nucleic acid sequence that encodes a protein having an amino acid sequence selected from the group consisting of SEQ ID NOs: 30, 31, 32, 33 and 34, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention includes and provides a method of producing a plant containing an expressed HES1 protein or fragment thereof in a plant comprising: (A) transforming the plant with a functional nucleic acid molecule, wherein the functional nucleic acid molecule comprises a promoter region, wherein the promoter region is linked to a structural region, wherein the structural region comprises a nucleic acid sequence that encodes a plant HES1 protein, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention includes and provides a method for reducing expression of a HES1 protein in a plant comprising: (A) transforming a plant with a nucleic acid molecule, the nucleic acid molecule having an exogenous promoter region which functions in plant cells to cause the production of a mRNA molecule, wherein the exogenous promoter region is linked to a transcribed nucleic acid molecule having a transcribed strand and a non-transcribed strand, wherein the transcribed strand is complementary to a nucleic acid molecule having a nucleic acid sequence selected from the group consisting of SEQ ID NOs: 1, 2, 3, 4, 6, 7, 8, 9, 10, 11, 12, 13, 14, 15, 16, 17, 18, 19, 20, 21, 23, 24, 25, 26, 27, 28, and 29 or fragment thereof; and wherein the transcribed nucleic acid molecule is linked to a 3' non-translated sequence that functions in the plant cells to cause termination of transcription and addition of polyadenylated ribonucleotides to the 3' end of the mRNA sequence; and (B) growing the transformed plant.

The present invention includes and provides a method for screening for increased phytosterol levels in a plant comprising interrogating genomic DNA for the presence or absence of a marker molecule that specifically hybridizes to a nucleic acid molecule having a nucleic acid sequence selected from the group consisting of SEQ ID NOs: 1, 2, 3, 4, 6, 7, 8, 9, 10, 11, 12, 13, 14, 15, 16, 17, 18, 19, 20, 21, 23, 24, 25, 26, 27, 28, and 29 or complements thereof; and detecting the presence or absence of the marker.

The present invention includes and provides a method for determining a genomic polymorphism in a plant that is predictive of increased phtosterol levels comprising the steps: (A) incubating a marker nucleic acid molecule, under conditions permitting nucleic acid hybridization, and a complementary nucleic acid molecule obtained from the plant, wherein the marker nucleic acid molecule specifically hybridizes to a nucleic acid molecule having a nucleic acid sequence selected from the group consisting of SEQ ID Nos:1, 2, 3, 4, 6, 7, 8, 9, 10, 11, 12, 13, 14, 15, 16, 17, 18, 19, 20, 21, 23, 24, 25, 26, 27, 28, and 29 or complements thereof; (B) permitting hybridization between the marker nucleic acid molecule and the complementary nucleic acid molecule obtained from the plant; and (C) detecting the presence of the polymorphism.

The present invention includes and provides a method for determining a level or pattern of HES1 expression in a plant comprising: (A) incubating under conditions permitting nucleic acid hybridization: a marker nucleic acid molecule, the marker nucleic acid molecule having a nucleic acid sequence selected from the group consisting of SEQ ID Nos: 1, 2, 3, 4, 6, 7, 8, 9, 10, 11, 12, 13, 14, 15, 16, 17, 18, 19, 20, 21, 23, 24, 25, 26, 27, 28, and 29 or complements thereof, with a complementary nucleic acid molecule obtained from a plant cell or plant tissue, wherein nucleic acid hybridization between the marker nucleic acid molecule; (B) permitting hybridization between the marker nucleic acid molecule and the complementary nucleic acid molecule obtained from the plant; and (C) detecting the level or pattern of the complementary nucleic acid, wherein the detection of the complementary nucleic acid is predictive of the level or pattern of the HES1 protein.

The present invention includes and provides a method for determining a level or pattern of a HES1 in a plant cell or plant tissue under evaluation which comprises assaying the concentration of a molecule, whose concentration is dependent upon the expression of a gene, said gene having a nucleic acid sequence which specifically hybridizes to a nucleic acid molecule having a nucleic acid sequence selected from the group consisting of SEQ ID Nos: 1, 2, 3, 4, 6, 7, 8, 9, 10, 11, 12, 13, 14, 15, 16, 17, 18, 19, 20, 21, 23, 24, 25, 26, 27, 28, and 29 or complements thereof, said molecule being present in the plant cell or plant tissue, in comparison to the concentration of that molecule present in a plant cell or plant tissue with a known level or pattern of said HES1 protein, wherein the assayed concentration of said molecule is compared to the assayed concentration of said molecule in the plant cell or plant tissue with a known level or pattern of said HES1 protein.

DESCRIPTION OF THE NUCLEIC AND AMINO ACID SEQUENCES

SEQ ID NO: 1 sets forth the nucleotide sequence of a soybean HES1 homolog.

SEQ ID NO: 2 sets forth the nucleotide sequence of a soybean HES1 homolog.

SEQ ID NO: 3 sets forth the nucleotide sequence of a soybean HES1 homolog.

SEQ ID NO: 4 sets forth the nucleotide sequence of a maize HES1 homolog.

SEQ ID NO: 5 sets forth the nucleotide sequence of a *Saccharomyces cerevisiae* HES1 homolog;

SEQ ID NO: 6 sets forth the partial nucleotide sequence of a soybean HES1 homolog;

SEQ ID NO: 7 sets forth the partial nucleotide sequence of a soybean HES1 homolog;

SEQ ID NO: 8 sets forth the partial nucleotide sequence of a soybean HES1 homolog;

SEQ ID NO: 9 sets forth the partial nucleotide sequence of a soybean HES1 homolog;

SEQ ID NO: 10 sets forth the partial nucleotide sequence of a soybean HES1 homolog. SEQ ID NO: 11 sets forth the partial nucleotide sequence of a soybean HES1 homolog.

SEQ ID NO: 12 sets forth the partial nucleotide sequence of a soybean HES1 homolog SEQ ID NO: 13 sets forth the partial nucleotide sequence of a soybean HES1 homolog;

SEQ ID NO: 14 sets forth the partial nucleotide sequence of a soybean HES1 homolog;

SEQ ID NO: 15 sets forth the partial nucleotide sequence of a soybean HES1 homolog;

SEQ ID NO: 16 sets forth the partial nucleotide sequence of a soybean HES1 homolog. SEQ ID NO: 17 sets forth the partial nucleotide sequence of a soybean HES1 homolog.

SEQ ID NO: 18 sets forth the partial nucleotide sequence of a soybean HES1 homolog.

SEQ ID NO: 19 sets forth the partial nucleotide sequence of a soybean HES1 homolog.

SEQ ID NO: 20 sets forth the partial nucleotide sequence of a soybean HES1 homolog.

SEQ ID NO: 21 sets forth the partial nucleotide sequence of an *Arabidopsis thaliana* HES1 homolog;

SEQ ID NO: 22 sets forth the partial nucleotide sequence of an *Arabidopsis thaliana* HES1 homolog.

SEQ ID NO: 23 sets forth the partial nucleotide sequence of an *Arabidopsis thaliana* HES1 homolog.

SEQ ID NO: 24 sets forth the partial nucleotide sequence of an *Arabidopsis thaliana* HES1 homolog.

SEQ ID NO: 25 sets forth the partial nucleotide sequence of an *Arabidopsis thaliana* HES1 homolog.

SEQ ID NO: 26 sets forth the partial nucleotide sequence of an *Arabidopsis thaliana* HES1 homolog.

SEQ ID NO: 27 sets forth the partial nucleotide sequence of an *Arabidopsis thaliana* HES1 homolog.

SEQ ID NO: 28 sets forth the partial nucleotide sequence of an *Arabidopsis thaliana* HES1 homolog.

SEQ ID NO: 29 sets forth the partial nucleotide sequence of an *Arabidopsis thaliana* HES1 homolog.

SEQ ID NO: 30 sets forth the amino acid sequences derived from a soybean HES1 gene.

SEQ ID NO: 31 sets forth the amino acid sequences derived from a soybean HES1 gene.

SEQ ID NO: 32 sets forth the amino acid sequences derived from a soybean HES1 gene.

SEQ ID NO: 33 sets forth the amino acid sequences derived from a maize HES1 gene.

SEQ ID NO: 34 sets forth the amino acid sequences derived from a *Saccharomyces cerevisiae* HES1 gene.

DETAILED DESCRIPTION

Utilizing a methodology that allows for the identification of genes that can influence phytosterol levels, plant HES1 genes were identified and isolated. HES1 are oxysterol-binding proteins. Overexpression of HES1 proteins in organisms can result in increased sterol levels in a variety of organisms. Moreover, the present invention provides a number of agents, for example, nucleic acid molecules encoding a plant HES1, and provides uses of such agents.

Agents:

The agents of the invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the invention may also be recombinant. As used herein, the term recombinant means any agent (e.g., DNA, peptide etc.), that is, or results, however indirect, from human manipulation of a nucleic acid molecule.

It is understood that the agents of the invention may be labeled with reagents that facilitate detection of the agent (e.g., fluorescent labels, Prober et al., *Science* 238:336–340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448).

(a) Nucleic Acid Molecules

Agents of the invention include nucleic acid molecules. In a preferred aspect of the present invention the nucleic acid molecule comprises a nucleic acid sequence which encodes a HES1 protein. In a preferred embodiment, the HES1 protein is derived from a plant. In another preferred embodiment, the HES1 protein is derived from a yeast. Examples of HES1 proteins are those encoded by a nucleic acid sequence having SEQ ID NO: 30, 31, 32, 33 or 34.

In another preferred embodiment, the nucleic molecule encodes a HES1 protein, preferably a yeast or plant HES1 protein comprising an oxysterol-binding protein consensus sequence—E(K, Q)xSH(H, R)PPx(S, T, A, C, F)A In another preferred aspect of the present invention the nucleic acid molecule comprises a nucleic acid sequence selected from SEQ ID NOs: 1–4, 6–29 or complements thereof or fragment of either. In another preferred aspect of the present invention the nucleic acid molecules of the present invention comprise nucleic acid sequences that encode a protein having an amino acid sequence of SEQ ID NO: 30, 31, 32, or 33 or fragment thereof.

It is understood that in a further aspect of the nucleic acid sequences of the present invention can encode a protein which differs from any of the proteins in that amino acid have been deleted, substituted or added without altering the function. For example, it is understood that codons capable of coding for such conservative amino acid substitutions are known in the art.

One subset of the nucleic acid molecules of the invention is fragment nucleic acids molecules. Fragment nucleic acid molecules may consist of significant portion(s) of, or indeed most of, the nucleic acid molecules of the invention, such as those specifically disclosed. Alternatively, the fragments may comprise smaller oligonucleotides (having from about 15 to about 400 nucleotide residues and more preferably, about 15 to about 30 nucleotide residues, or about 50 to about 100 nucleotide residues, or about 100 to about 200 nucleotide residues, or about 200 to about 400 nucleotide residues, or about 275 to about 350 nucleotide residues).

A fragment of one or more of the nucleic acid molecules of the invention may be a probe and specifically a PCR probe. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (available on the worldwide web at genome.wi.mit.edu/cgi-bin/primer/primer3.cgi), STSPipeline (available on the worldwide web at genome.wi.mit.edu/cgi-bin/www-STS_Pipeline), or GeneUp (Pesole et al., BioTechniques 25:112–123 (1998)), for example, can be used to identify potential PCR primers.

Another subset of the nucleic acid molecules of the invention include nucleic acid molecules that encode a protein or fragment thereof.

Nucleic acid molecules or fragments thereof of the present invention are capable of specifically hybridizing to other nucleic acid molecules under certain circumstances. Nucleic acid molecules of the present invention include those that specifically hybridize to nucleic acid molecules having a nucleic acid sequence selected from the group consisting of SEQ ID NOs: 1–4, 6–29 or complements thereof.

As used herein, two nucleic acid molecules are said to be capable of specifically hybridizing to one another if the two molecules are capable of forming an anti-parallel, double-stranded nucleic acid structure.

A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning, A Laboratory Manual*, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization are, for example, 6.0× sodium chloride/sodium citrate (SSC) at about 45° C., followed by a wash of 2.0× SSC at 20–25° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0× SSC at 20–25° C. to a high stringency of about 0.2× SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID Nos: 1–4, 6–29 or complements thereof under moderately stringent conditions, for example at about 2.0× SSC and about 65° C.

In a particularly preferred embodiment, a nucleic acid of the present invention will include those nucleic acid molecules that specifically hybridize to one or more of the nucleic acid molecules set forth in SEQ ID NOs: 1–4, 6–29 or complements thereof under high stringency conditions such as 0.2× SSC and about 65° C.

In a particular preferred embodiment, a nucleic acid molecule of the present invention specifically hybridizes to a nucleic acid molecule having a nucleic acid sequence selected from the group SEQ ID Nos; 1–4, 6–29 or complements thereof but does not hybridize to a nucleic acid molecule having a nucleic acid sequenc of SEQ ID NO: 5 or complement thereof under the same conditions.

In one aspect of the present invention, the nucleic acid molecules of the present invention have one or more of the nucleic acid sequences set forth in SEQ ID NOs: 1–4, 6–29 or complements thereof.

In another aspect of the present invention, one or more of the nucleic acid molecules of the present invention share between 100% and 90% sequence identity with one or more of the nucleic acid sequences set forth in SEQ ID NOs: 1–4, 6–29 or complements thereof. In a further aspect of the present invention, one or more of the nucleic acid molecules of the present invention share between 100% and 95% sequence identity with one or more of the nucleic acid sequences set forth in SEQ ID NOs: 1–4, 6–29 or complements thereof. In a more preferred aspect of the present invention, one or more of the nucleic acid molecules of the present invention share between 100% and 98% sequence identity with one or more of the nucleic acid sequences set forth in SEQ ID NOs: 1–4, 6–29 or complements thereof. In an even more preferred aspect of the present invention, one or more of the nucleic acid molecules of the present invention share between 100% and 99% sequence identity with one or more of the sequences set forth in SEQ ID NOs: 1–4, 6–29 or complements thereof.

In a preferred embodiment the percent identity calculations are performed using the Megalign program of the LASERGENE bioinformatics computing suite (default parameters, DNASTAR Inc., Madison, Wis.).

A nucleic acid molecule of the invention can also encode a homolog protein. As used herein, a homolog protein molecule or fragment thereof is a counterpart protein molecule or fragment thereof in a second species (e.g., maize HES1 is a homolog of *Arabidopsis* HES1). A homolog can also be generated by molecular evolution or DNA shuffling techniques, so that the molecule retains at least one functional or structure characteristic of the original protein (see, for example, U.S. Pat. No. 5,811,238). Particularly preferred homologs are selected from the group consisting of alfalfa, *Arabidopsis*, barley, *Brassica*, broccoli, cabbage, citrus, cotton, garlic, oat, oilseed rape, onion, canola, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, soybean, maize, and *Phaseolus*. More particularly, preferred homologs are selected from maize, canola, soybean, *crambe*, mustard, castor bean, peanut, sesame, cottonseed, linseed, safflower, oil palm, flax and sunflower.

In a preferred embodiment, nucleic acid molecules having SEQ ID Nos: 1–4, 6–29 or complements thereof and fragments of either can be utilized to obtain such homologs.

In another further aspect of the present invention, nucleic acid molecules of the present invention can comprise sequences, which differ from those encoding a protein or fragment thereof in SEQ ID NOs: 30, 31, 32, and 33 due to fact that the different nucleic acid sequence encodes a protein having one or more conservative amino acid changes. It is understood that codons capable of coding for such conservative amino acid substitutions are known in the art.

It is well known in the art that one or more amino acids in a native sequence can be substituted with other amino acid(s), the charge and polarity of which are similar to that of the native amino acid, i.e., a conservative amino acid substitution, resulting in a silent change. Conservative substitutes for an amino acid within the native polypeptide sequence can be selected from other members of the class to which the amino acid belongs. Amino acids can be divided into the following four groups: (1) acidic amino acids, (2) basic amino acids, (3) neutral polar amino acids, and (4) neutral, nonpolar amino acids. Representative amino acids within these various groups include, but are not limited to, (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral nonpolar (hydrophobic) amino acids such as alanine, leucine, isoleucine, valine, proline, phenylalanine, tryptophan, and methionine.

Conservative amino acid substitution within the native polypeptide sequence can be made by replacing one amino acid from within one of these groups with another amino acid from within the same group. In a preferred aspect, biologically functional equivalents of the proteins or fragments thereof of the present invention can have ten or fewer conservative amino acid changes, more preferably seven or fewer conservative amino acid changes, and most preferably five or fewer conservative amino acid changes. The encoding nucleotide sequence will thus have corresponding base substitutions, permitting it to encode biologically functional equivalent forms of the proteins or fragments of the present invention.

It is understood that certain amino acids may be substituted for other amino acids in a protein structure without appreciable loss of interactive binding capacity with structures such as, for example, antigen-binding regions of antibodies or binding sites on substrate molecules. Because it is the interactive capacity and nature of a protein that defines that protein's biological functional activity, certain amino acid sequence substitutions can be made in a protein sequence and, of course, its underlying DNA coding sequence and, nevertheless, a protein with like properties can still be obtained. It is thus contemplated by the inventors that various changes may be made in the peptide sequences of the proteins or fragments of the present invention, or corresponding DNA sequences that encode said peptides, without appreciable loss of their biological utility or activity. It is understood that codons capable of coding for such amino acid changes are known in the art.

In making such changes, the hydropathic index of amino acids may be considered. The importance of the hydropathic amino acid index in conferring interactive biological function on a protein is generally understood in the art (Kyte and Doolittle, *J. Mol. Biol.* 157, 105–132 (1982), the entirety of which is herein incorporated by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, *J. Mol. Biol.* 157:105–132 (1982)); these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (4.5).

In making such changes, the substitution of amino acids whose hydropathic indices are within ±2 is preferred, those which are within +1 are particularly preferred, and those within ±0.5 are even more particularly preferred.

It is also understood in the art that the substitution of like amino acids can be made effectively on the basis of hydrophilicity. U.S. Pat. No. 4,554,101 states that the greatest local average hydrophilicity of a protein, as govern by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4).

In making such changes, the substitution of amino acids whose hydrophilicity values are within ±2 is preferred, those which are within ±1 are particularly preferred, and those within ±0.5 are even more particularly preferred.

In a further aspect of the present invention, one or more of the nucleic acid molecules of the present invention differ in nucleic acid sequence from those encoding a protein or fragment thereof due to the fact that one or more codons encoding an amino acid has been substituted for a codon that encodes a nonessential substitution of the amino acid originally encoded.

Agents of the invention include nucleic acid molecules that encode at least about a contiguous 10 amino acid region of a protein of the present invention, more preferably at least about a contiguous 25, 40, 50, 100, or 125 amino acid region of a protein of the present invention.

(b) Protein and Peptide Molecules

A class of agents includes one or more of the protein or fragments thereof or peptide molecules encoded by a nucleic acid molecule having a nucleic acid sequence selected from the group consisting of SEQ ID NO: 30, 31, 32, and 33 or fragments thereof or one or more of the protein or fragment thereof and peptide molecules encoded by other nucleic acid agents of the invention.

A further particularly preferred class of protein is a plant HES1 protein. A further particularly preferred class of protein is a yeast HES1 protein.

As used herein, the term "protein" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein" or "peptide molecule" includes any protein that is modified by any biological or non-biological process. The terms "amino acid" and "amino acids" refer to all naturally occurring L-amino acids. This definition is meant to include norleucine, norvaline, ornithine, homocysteine, and homoserine.

One or more of the protein or fragments thereof or peptide molecules may be produced via chemical synthesis, or more preferably, by expression in a suitable bacterial or eukaryotic host. Suitable methods for expression are described by Sambrook et al., In: *Molecular Cloning, A Laboratory Manual, 2nd Edition*, Cold Spring Harbor Press, Cold Spring Harbor, N.Y. (1989), the entirety of which is herein incorporated by reference, or similar texts.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the invention are preferably produced via recombinant means.

Another class of agents comprise protein or peptide molecules or fragments or fusions thereof comprising SEQ ID NO: 30, 31, 32, or 33 or fragment thereof or encoded by SEQ ID NO: 1, 2, 3, or 4 in which conservative, non-essential or non-relevant amino acid residues have been added, replaced or deleted. Another particular preferred class of proteins are those having an amino acid sequence where the nucleic acid sequence is selected from the group consisting of SEQ ID NOs: 6–29 in which conservative, non-essential or non-relevant amino acid residues have been added, replaced or deleted. A further particularly preferred class of protein is a HES1 protein in which conservative, non-essential or non-relevant amino acid residues have been added, replaced or deleted. Computerized means for designing modifications in protein structure are known in the art (Dahiyat and Mayo, *Science* 278:82–87 (1997), the entirety of which is herein incorporated by reference).

A protein of the invention can also be a homolog protein. As used herein, a homolog protein or fragment thereof is a counterpart protein or fragment thereof in a second species. A homolog can also be generated by molecular evolution or DNA shuffling techniques, so that the molecule retains at least one functional or structure characteristic of the original (see, for example, U.S. Pat. No. 5,811,238, the entirety of which is herein incorporated by reference).

Particularly preferred homologs are selected from the group consisting of alfalfa, *Arabidopsis*, barley, *Brassica*, broccoli, cabbage, citrus, cotton, garlic, oat, oilseed rape, onion, canola, flax, an ornamental plant, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, and *Phaseolus*. Other particularly preferred homologs are selected from the group consisting of blue green algae and bacteria. In a more preferred embodiment, the homologs are selected from the group of maize and soybean.

In a preferred embodiment, the nucleic acid molecules of the present invention or complements and fragments of either can be utilized to obtain such homologs.

The degeneracy of the genetic code, which allows different nucleic acid sequences to code for the same protein or peptide, is known in the literature (U.S. Pat. No. 4,757,006, the entirety of which is herein incorporated by reference).

Agents of the invention include proteins comprising at least about a contiguous 10 amino acid region preferably comprising at least about a contiguous 20 amino acid region, even more preferably comprising at least a contiguous 25, 35, 50, 75 or 100 amino acid region of a protein of the present invention. In another preferred embodiment, the proteins of the present invention include between about 10 and about 25 contiguous amino acid region, more preferably between about 20 and about 50 contiguous amino acid region, and even more preferably between about 40 and about 80 contiguous amino acid region.

(c) Plant Constructs and Plant Transformants

One or more of the nucleic acid molecules of the invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. In a preferred embodiment, the exogenous genetic material includes a nucleic acid molecule of the present invention, preferably a nucleic acid molecule having a sequence selected from the group consisting of SEQ ID NOs: 1–29 or complements thereof or fragments of either. Another preferred class of exogenous genetic material is nucleic acid molecules that encode a protein or fragment thereof having an amino acid selected from the group consisting of SEQ ID NOs: 30, 31, 32, 33, and 34 or fragments thereof.

In another preferred aspect of the present invention, exogenous genetic material is nucleic acid molecules that comprise a nucleic acid sequence which encodes a HES1 protein or fragment thereof, more preferably a yeast HES1 protein or fragment thereof, even more preferably a plant HES1 protein or fragment thereof.

Such genetic material may be transferred into either monocotyledons and dicotyledons including, but not limited to maize, soybean, *Arabidopsis, phaseolus*, peanut, alfalfa, wheat, rice, oat, sorghum, rye, tritordeum, millet, fescue, perennial ryegrass, sugarcane, cranberry, papaya, banana, banana, muskmelon, apple, cucumber, dendrobium, gladiolus, chrysanthemum, liliacea, cotton, eucalyptus, sunflower, canola, turfgrass, sugarbeet, coffee and dioscorea (Christou, In: *Particle Bombardment for Genetic Engineering of Plants*, Biotechnology Intelligence Unit. Academic Press, San Diego, Calif. (1996), the entirety of which is herein incorporated by reference). Particularly preferred plants are selected from maize, canola, soybean, *Crambe*, mustard, castor bean, peanut, sesame, cottonseed, linseed, safflower, oil palm, flax and sunflower.

Transfer of a nucleic acid that encodes a protein can result in expression or overexpression of that protein in a transformed cell or transgenic plant. One or more of the proteins or fragments thereof encoded by nucleic acid molecules of the invention may be overexpressed in a transformed cell or transformed plant. Such expression or overexpression may be the result of transient or stable transfer of the exogenous genetic material.

In a preferred embodiment, expression or overexpression of a HES1 protein in a plant provides in that plant, relative to an untransformed plant with a similar genetic background, an increased level of phytosterols.

In a preferred embodiment, expression or overexpression of a HES1 protein in a plant provides in that plant, relative to an untransformed plant with a similar genetic background, an altered composition of phytosterols.

In another embodiment, overexpression of a HES1 protein in a plant provides in that plant, relative to an untransformed plant with a similar genetic background, an increased level of a HES1 protein in a plastid.

In another preferred embodiment, overexpression of the HES1 protein in a transformed plant will result in a plant which provides when eaten acts exhibits an increased ability to act as a cholesterol lowering agent relative to an untransformed plant with a similar genetic background.

Exogenous genetic material may be transferred into a host cell by the use of a DNA vector or construct designed for such a purpose. Design of such a vector is generally within the skill of the art (See, *Plant Molecular Biology: A Laboratory Manual*, Clark (ed.), Springer, New York (1997), the entirety of which is herein incorporated by reference).

A construct or vector may include a plant promoter to express the protein or protein fragment of choice. A number of promoters, which are active in plant cells, have been described in the literature. These include the nopaline synthase (NOS) promoter (Ebert et al., *Proc. Natl. Acad. Sci.* (U.S.A.) 84:5745–5749 (1987), the entirety of which is herein incorporated by reference), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315–324 (1987), the entirety of which is herein incorporated by reference) and the CaMV 35S promoter (Odell et al., *Nature* 313: 810–812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (U.S.A.) 84:6624–6628 (1987), the entirety of which is herein incorporated by reference), the sucrose synthase promoter (Yang et al., *Proc. Natl. Acad. Sci.* (U.S.A.) 87:41444148 (1990), the entirety of which is herein incorporated by reference), the R gene complex promoter (Chandler et al., *The Plant Cell* 1:1175–1183 (1989), the entirety of which is herein incorporated by reference) and the chlorophyll a/b binding protein gene promoter, etc. These promoters have been used to create DNA constructs that have been expressed in plants; see, e.g., PCT publication WO 84/02913. The CaMV 35S promoters are preferred for use in plants. Promoters known or found to cause transcription of DNA in plant cells can be used in the invention.

For the purpose of expression in source tissues of the plant, such as the leaf, seed, root or stem, it is preferred that the promoters utilized have relatively high expression in these specific tissues. Tissue-specific expression of a protein of the present invention is a particularly preferred embodiment. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci.* (U.S.) 87:3459–3463 (1990), the entirety of which is herein incorporated by reference), the chloroplast fructose-1,6-biphosphatase (FBPase) promoter from wheat (Lloyd et al., *Mol. Gen. Genet.* 225:209–216 (1991), the entirety of which is herein incorporated by reference), the nuclear photosynthetic ST-LS 1 promoter from potato (Stockhaus et al., *EMBO J.* 8:2445–2451 (1989), the entirety of which is herein incorporated by reference), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773–778 (1994), the entirety of which is herein incorporated by reference), the promoter for the Cab-1 gene from wheat (Fejes et al., *Plant Mol. Biol.* 15:921–932 (1990), the entirety of which is herein incorporated by reference), the promoter for the CAB-1 gene from spinach (Lubberstedt et al., *Plant Physiol.* 104:997–1006 (1994), the entirety of which is herein incorporated by reference), the promoter for the cab1R gene from rice (Luan et al., *Plant Cell.* 4:971–981 (1992), the entirety of which is herein incorporated by reference), the pyruvate, orthophosphate dikinase (PPDK) promoter from maize (Matsuoka et al., *Proc. Natl. Acad. Sci.* (U.S.A.) 90: 9586–9590 (1993), the entirety of which is herein incorporated by reference), the promoter for the tobacco Lhcb1*2 gene (Cerdan et al., *Plant Mol. Biol.* 33:245–255 (1997), the entirety of which is herein incorporated by reference), the *Arabidopsis thaliana* SUC2 sucrose-H+ symporter promoter (Truernit et al., *Planta.* 196:564–570 (1995), the entirety of which is herein incorporated by reference) and the promoter for the thylakoid membrane proteins from spinach (psaD, psaF, psaE, PC, FNR, atpC, atpD, cab, rbcS). Other promoters for the chlorophyll a/b-binding proteins may also be utilized in the invention, such as the promoters for LhcB gene and PsbP gene from white mustard (*Sinapis alba*; Kretsch et al., *Plant Mol. Biol.* 28:219–229 (1995), the entirety of which is herein incorporated by reference).

For the purpose of expression in sink tissues of the plant, such as the tuber of the potato plant, the fruit of tomato, or the seed of maize, wheat, rice and barley, it is preferred that the promoters utilized in the invention have relatively high expression in these specific tissues. A number of promoters for genes with tuber-specific or tuber-enhanced expression are known, including the class I patatin promoter (Bevan et al., *EMBO J.* 8:1899–1906 (1986); Jefferson et al., *Plant Mol. Biol.* 14:995–1006 (1990)), the promoter for the potato tuber ADPGPP genes, both the large and small subunits, the sucrose synthase promoter (Salanoubat and Belliard, *Gene* 60:47–56 (1987), Salanoubat and Belliard, *Gene* 84:181–185 (1989), both of which are herein incorporated by reference in their entirety), the promoter for the major tuber proteins including the 22 kd protein complexes and protease inhibitors (Hannapel, *Plant Physiol.* 101:703–704 (1993), the entirety of which is herein incorporated by reference), the promoter for the granule-bound starch synthase gene (GBSS) (Visser et al., *Plant Mol. Biol.* 17:691–699 (1991), the entirety of which is herein incorporated by reference) and other class I and II patatins promoters (Koster-Topfer et al., *Mol Gen Genet.* 219:390–396 (1989); Mignery et al., *Gene.* 62:2744 (1988), both of which are herein incorporated by reference in their entirety).

Other promoters can also be used to express a protein or fragment thereof in specific tissues, such as seeds or fruits. The promoter for β-conglycinin (Chen et al., *Dev. Genet.* 10: 112–122 (1989), the entirety of which is herein incorporated by reference) or other seed-specific promoters such as the napin and phaseolin promoters, can be used. The zeins are a group of storage proteins found in maize endosperm. Genomic clones for zein genes have been isolated (Pedersen et al., *Cell* 29:1015–1026 (1982), the entirety of which is herein incorporated by reference) and the promoters from these clones, including the 15 kD, 16 kD, 19 kD, 22 kD, 27 kD and genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell Biol.* 13:5829–5842 (1993), the entirety of which is herein incorporated by reference). Examples of promoters suitable for expression in wheat include those promoters for the ADP-glucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene (Samac et al., *Plant Mol. Biol.* 25:587–596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci. (U.S.A.)* 86:7890–7894 (1989), the entirety of which is herein incorporated by reference). Other root cell specific promoters include those reported by Conkling et al. (Conkling et al., *Plant Physiol.* 93:1203–1211 (1990), the entirety of which is herein incorporated by reference).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are herein incorporated by reference in their entirety. In addition, a tissue specific enhancer may be used (Fromm et al., *The Plant Cell* 1:977–984 (1989), the entirety of which is herein incorporated by reference).

Constructs or vectors may also include, with the coding region of interest, a nucleic acid sequence that acts, in whole or in part, to terminate transcription of that region. A number of such sequences have been isolated, including the Tr7 3' sequence and the NOS 3' sequence (Ingelbrecht et al., *The Plant Cell* 1:671–680 (1989); Bevan et al., *Nucleic Acids Res.* 11:369–385 (1983), both of which are herein incorporated by reference in their entirety).

A vector or construct may also include regulatory elements. Examples of such include the Adh intron 1 (Callis et al., *Genes and Develop.* 1:1183–1200 (1987), the entirety of which is herein incorporated by reference), the sucrose synthase intron (Vasil et al., *Plant Physiol.* 91:1575–1579 (1989), the entirety of which is herein incorporated by reference) and the TMV omega element (Gallie et al., *The Plant Cell* 1:301–311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to: a neo gene (Potrykus et al., *Mol. Gen. Genet.* 199:183–188 (1985), the entirety of which is herein incorporated by reference), which codes for kanamycin resistance and can be selected for using kanamycin, G418, etc.; a bar gene which codes for bialaphos resistance; a mutant EPSP synthase gene (Hinchee et al., *Bio/Technology* 6:915–922 (1988), the entirety of which is herein incorporated by reference) which encodes glyphosate resistance; a nitrilase gene which confers resistance to bromoxynil (Stalker et al., *J. Biol. Chem.* 263:6310–6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500–12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393405 (1996), the entirety of which is herein incorporated by reference.

A vector or construct may also include a screenable marker. Screenable markers may be used to monitor expression. Exemplary screenable markers include: a β-glucuronidase or uidA gene (GUS) which encodes an enzyme for which various chromogenic substrates are known (Jefferson, *Plant Mol. Biol. Rep.* 5:387–405 (1987); Jefferson et al., *EMBO J.* 6:3901–3907 (1987), both of which are herein incorporated by reference in their entirety); an R-locus gene, which encodes a product that regulates the production of anthocyanin pigments (red color) in plant tissues (Dellaporta et al., Stadler Symposium 11:263–282 (1988), both of which are herein incorporated by reference in their entirety); a β-lactamase gene (Sutcliffe et al., *Proc. Natl. Acad. Sci. (U.S.A.)* 75:3737–3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234:856–859 (1986), the entirety of which is herein incorporated by reference); a xylE gene (Zukowsky et al., *Proc. Natl. Acad. Sci. (U.S.A.)* 80:1101–1105 (1983), the entirety of which is herein incorporated by reference) which encodes a catechol dioxygenase that can convert chromogenic catechols; an α-amylase gene (Ikatu et al., *Bio/Technol.* 8:241–242 (1990), the entirety of which is herein incorporated by reference); a tyrosinase gene (Katz et al., *J. Gen. Microbiol.* 129:2703–2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205–225 (1991); Vasil, *Plant Mol. Biol.* 25:925–937 (1994), both of which are herein incorporated by reference in their entirety). For example, electroporation has been used to transform maize protoplasts (Fromm et al., *Nature* 312: 791–793 (1986), the entirety of which is herein incorporated by reference).

Other vector systems suitable for introducing transforming DNA into a host plant cell include but are not limited to binary artificial chromosome (BIBAC) vectors (Hamilton et al., *Gene* 200:107–116 (1997), the entirety of which is herein incorporated by reference); and transfection with RNA viral vectors (Della-Cioppa et al., *Ann. N.Y. Acad. Sci.* (1996), 792 (Engineering Plants for Commercial Products and Applications), 57–61, the entirety of which is herein incorporated by reference). Additional vector systems also include plant selectable YAC vectors such as those described in Mullen et al., *Molecular Breeding* 4:449457 (1988), the entirety of which is herein incorporated by reference.

Technology for introduction of DNA into cells is well known to those of skill in the art. Four general methods for delivering a gene into cells have been described: (1) chemical methods (Graham and van der Eb, *Virology* 54:536–539 (1973), the entirety of which is herein incorporated by reference); (2) physical methods such as microinjection (Capecchi, *Cell* 22:479488 (1980), the entirety of which is herein incorporated by reference), electroporation (Wong and Neumann, *Biochem. Biophys. Res. Commun.* 107:584–587 (1982); Fromm et al., *Proc. Natl. Acad. Sci. (U.S.A.)* 82:5824–5828 (1985); U.S. Pat. No. 5,384,253, all of which are herein incorporated by reference in their entirety); the gene gun (Johnston and Tang, *Methods Cell Biol.* 43:353–365 (1994), the entirety of which is herein incorporated by reference); and vacuum infiltration (Bechtold et al., *C.R. Acad. Sci. Paris, Life Sci.* 316:1194–1199. (1993), the entirety of which is herein incorporated by reference); (3) viral vectors (Clapp, *Clin. Perinatol.* 20:155–168 (1993); Lu et al., *J. Exp. Med.* 178:2089–2096 (1993); Eglitis and Anderson, Biotechniques 6:608–614 (1988), all of which are herein incorporated by reference in their entirety); and (4) receptor-mediated mechanisms (Curiel et al., *Hum. Gen. Ther.* 3:147–154 (1992), Wagner et al., *Proc. Natl. Acad. Sci. (USA)* 89:6099–6103 (1992), both of which are herein incorporated by reference in their entirety).

Acceleration methods that may be used include, for example, microprojectile bombardment and the like. One example of a method for delivering transforming nucleic acid molecules into plant cells is microprojectile bombardment. This method has been reviewed by Yang and Christou (eds.), *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671–674 (1988), the entirety of which is herein incorporated by reference) nor the susceptibility to *Agrobacterium* infection is required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603–618 (1990), the entirety of which is herein incorporated by reference). The screen disperses the tungsten nucleic acid particles so that they are not delivered to the recipient cells in large aggregates. A particle delivery system suitable for use with the invention is the helium acceleration PDS-1000/He gun, which is available from Bio-Rad Laboratories (Bio-Rad, Hercules, Calif.) (Sanford et al., *Technique* 3:3–16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain 1000 or more loci of cells transiently expressing a marker gene. The number of cells in a focus which express the exogenous gene product 48 hours post-bombardment often ranges from one to ten, and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci.* (*U.S.A.*) 87:8526–8530 (1990); Svab and Maliga, *Proc. Natl. Acad. Sci.* (*U.S.A.*) 90:913–917 (1993); Staub and Maliga, *EMBO J.* 12:601–606 (1993); U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions that influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629–635 (1985) and Rogers et al., *Methods Enzymol.* 153:253–277 (1987), both of which are herein incorporated by reference in their entirety. Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179–203 (1985), the entirety of which is herein incorporated by reference). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes Rogers et al., *Methods Enzymol.* 153:253–277 (1987), the entirety of which is herein incorporated by reference). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant, transgenic plant that contains a single added gene, germinating some of the seed produced and analyzing the resulting plants produced for the gene of interest.

It is also to be understood that two different transgenic plants can also be mated to produce offspring that contain two independently segregating, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193–200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454457 (1988), all of which are herein incorporated by reference in their entirety).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor. Appl. Genet.* 205:34 (1986); Yamada et al., *Plant Cell Rep.* 4:85 (1986); Abdullah et al., *Biotechnology* 4:1087 (1986), all of which are herein incorporated by reference in their entirety).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988), the entirety of which is herein incorporated by reference). In addition, "particle gun" or high-velocity microprojectile technology can be utilized (Vasil et al., *Bio/Technology* 10:667 (1992), the entirety of which is herein incorporated by reference).

Using the latter technology, DNA is carried through the cell wall and into the cytoplasm on the surface of small metal particles as described (Klein et al., *Nature* 328:70 (1987); Klein et al., *Proc. Natl. Acad. Sci.* (*U.S.A.*) 85:8502–8505 (1988); McCabe et al., *Bio/Technology* 6:923 (1988), all of which are herein incorporated by reference in their entirety). The metal particles penetrate through several layers of cells and thus allow the transformation of cells within tissue explants.

Other methods of cell transformation can also be used and include but are not limited to introduction of DNA into plants by direct DNA transfer into pollen (Hess et al, *Intern Rev. Cytol.* 107:367 (1987); Luo et al., *Plant Mol. Biol. Reporter* 6:165 (1988), both of which are herein incorporated by reference in their entirety), by direct injection of DNA into reproductive organs of a plant (Pena et al., *Nature* 325:274 (1987), the entirety of which is herein incorporated by reference), or by direct injection of DNA into the cells of immature embryos followed by the rehydration of desiccated embryos (Neuhaus et al., *Theor. Appl. Genet.* 75:30 (1987), the entirety of which is herein incorporated by reference).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908, all of which are herein incorporated by reference in their entirety); soybean (U.S. Pat. No. 5,569,834; U.S. Pat. No. 5,416,011; McCabe et. al., *Biotechnology* 6:923 (1988); Christou et al., *Plant Physiol.* 87:671–674 (1988), all of which are herein incorporated by reference in their entirety); *Brassica* U.S. Pat. No. 5,463,174, the entirety of which is herein incorporated by reference); peanut (Cheng et al., *Plant Cell Rep.* 15:653–657 (1996), McKently et al, *Plant Cell Rep.* 14:699–703 (1995), both of which are herein incorporated by reference in their entirety); papaya; pea (Grant et al., *Plant Cell Rep.* 15:254–258 (1995), the entirety of which is herein incorporated by reference); and *Arabidopsis thaliana* (Bechtold et al., *C.R. Acad. Sci. Paris, Life Sci.* 316: 1194–1199. (1993), the entirety of which is herein incorporated by reference). The latter method for transforming *Arabidopsis thaliana* is commonly called "dipping" or vacuum infiltration or germplasm transformation.

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*USA*) 84:5354 (1987), the entirety of which is herein incorporated by reference); barley (Wan and Lemaux, *Plant Physiol* 104:37 (1994), the entirety of which is herein incorporated by reference); maize (Rhodes et al., *Science* 240:204 (1988); Gordon-Kamm et al., *Plant Cell* 2:603–618 (1990); Fromm et al., *Bio/Technology* 8:833 (1990); Koziel et al., *Bio/Technology* 11: 194 (1993); Armstrong et al., *Crop Science* 35:550–557 (1995), all of which are herein incorporated by reference in their entirety); oat (Somers et al., *Bio/Technology* 10:1589 (1992), the entirety of which is herein incorporated by reference); orchard grass (Horn et al., *Plant Cell Rep.* 7:469 (1988), the entirety of which is herein incorporated by reference); rice (Toriyama et al., *Theor Appl. Genet.* 205:34 (1986); Part et al., *Plant Mol. Biol.* 32:1135–1148 (1996); Abedinia et al., *Aust. J. Plant Physiol.* 24:133–141 (1997); Zhang and Wu, *Theor. Appl. Genet.* 76:835 (1988); Zhang et al., *Plant Cell Rep.* 7:379 (1988); Battraw and Hall, *Plant Sci.* 86:191–202 (1992); Christou et al., *Bio/Technology* 9:957 (1991), all of which are herein incorporated by reference in their entirety); rye (De la Pena et al., *Nature* 325:274 (1987), the entirety of which is herein incorporated by reference); sugarcane (Bower and Birch, *Plant J.* 2:409 (1992), the entirety of which is herein incorporated by reference); tall fescue (Wang et al., *Bio/Technology* 10:691 (1992), the entirety of which is herein incorporated by reference) and wheat (Vasil et al., *Bio/Technology* 10:667 (1992); U.S. Pat. No. 5,631,152, both of which are herein incorporated by reference in their entirety).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990), all of which are herein incorporated by reference in their entirety). Transient expression systems may be used to functionally dissect gene constructs (see generally, Mailga et al., *Methods in Plant Molecular Biology*, Cold Spring Harbor Press (1995), the entirety of which is herein incorporated by reference).

Any of the nucleic acid molecules of the invention may be introduced into a plant cell in a permanent or transient manner in combination with other genetic elements such as vectors, promoters, enhancers, etc. Further, any of the nucleic acid molecules of the invention may be introduced into a plant cell in a manner that allows for expression or overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279–289 (1990); van der Krol et al., *Plant Cell* 2:291–299 (1990), both of which are herein incorporated by reference in their entirety). Cosuppression may result from stable transformation with a single copy nucleic acid molecule that is homologous to a nucleic acid sequence found with the cell (Prolls and Meyer, *Plant J.* 2:465475 (1992), the entirety of which is herein incorporated by reference) or with multiple copies of a nucleic acid molecule that is homologous to a nucleic acid sequence found with the cell (Mittlesten et al., *Mol. Gen. Genet.* 244:325–330 (1994)). Genes, even though different, linked to homologous promoters may result in the cosuppression of the linked genes (Vaucheret, *C.R. Acad. Sci. III* 316:1471–1483 (1993); Flavell, *Proc. Natl. Acad. Sci.* (*U.S.A.*) 91:3490–3496 (1994)); van Blokland et al., *Plant J.* 6:861–877 (1994); Jorgensen, *Trends Biotechnol.* 8:340–344 (1990); Meins and Kunz, In: *Gene Inactivation and Homologous Recombination in Plants*, Paszkowski (ed.), pp. 335–348, Kluwer Academic, Netherlands (1994), all of which are herein incorporated by reference in their entirety).

It is understood that one or more of the nucleic acids of the invention may be introduced into a plant cell and transcribed using an appropriate promoter with such transcription resulting in the cosuppression of an endogenous protein.

Antisense approaches are a way of preventing or reducing gene function by targeting the genetic material (Mol et al., *FEBS Lett.* 268:427430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49–63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569–597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155–184 (1990), the entirety of which is herein incorporated by reference). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a protein in a plant cell may be reduced or depressed by growing a transformed plant cell containing a nucleic acid molecule of the present invnetion whose non-transcribed strand encodes a protein or fragment thereof.

Posttranscriptional gene silencing (PTGS) can result in virus immunity or gene silencing in plants. PTGS is induced by dsRNA and is mediated by an RNA-dependent RNA polymerase, present in the cytoplasm, that requires a dsRNA template. The dsRNA is formed by hybridization of complementary transgene mRNAs or complementary regions of the same transcript. Duplex formation can be accomplished by using transcripts from one sense gene and one antisense gene colocated in the plant genome, a single transcript that has self-complementarity, or sense and antisense transcripts from genes brought together by crossing. The dsRNA-dependent RNA polymerase makes a complementary strand from the transgene mRNA and RNAse molecules attach to this complementary strand (cRNA). These cRNARNase molecules hybridize to the endogene mRNA and cleave the single-stranded RNA adjacent to the hybrid. The cleaved single-stranded RNAs are further degraded by other host RNases because one will lack a capped 5' end and the other will lack a poly(A) tail (Waterhouse et al., *PNAS* 95: 13959–13964 (1998)).

It is understood that one or more of the nucleic acids of the invention may be introduced into a plant cell and transcribed using an appropriate promoter with such transcription resulting in the postranscriptional gene silencing of an endogenous transcript.

Antibodies have been expressed in plants (Hiatt et al., *Nature* 342:76–78 (1989); Conrad and Fielder, *Plant Mol. Biol.* 26:1023–1030 (1994), both of which are herein incorporated by reference in their entirety). Cytoplasmic expression of a scFv (single-chain Fv antibody) has been reported to delay infection by artichoke mottled crinkle virus. Transgenic plants that express antibodies directed against endogenous proteins may exhibit a physiological effect (Philips et al., *EMBO J.* 16:4489–4496 (1997); Marion-Poll, *Trends in Plant Science* 2:447–448 (1997), both of which are herein incorporated by reference in their entirety). For example, expressed anti-abscisic antibodies have been reported to result in a general perturbation of seed development (Philips et al., *EMBO J.* 16: 44894496 (1997), the entirety of which is herein incorporated by reference).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313–1315 (1997); Baca et al., *Ann. Rev. Biophys. Biomol. Struct.* 26:461–493 (1997), both of which are herein incorporated by reference in their entirety). The catalytic abilities of abzymes may be enhanced by site directed mutagenesis. Examples of abzymes are, for example, set forth in U.S. Pat. No. 5,658,753; U.S. Pat. No. 5,632,990; U.S. Pat. No. 5,631,137; U.S. Pat. No. 5,602,015; U.S. Pat. No. 5,559,538; U.S. Pat. No. 5,576,174; U.S. Pat. No. 5,500,358; U.S. Pat. No. 5,318,897; U.S. Pat. No. 5,298,409; U.S. Pat. No. 5,258,289 and U.S. Pat. No. 5,194,585, all of which are herein incorporated by reference in their entirety.

It is understood that any of the antibodies of the invention may be expressed in plants and that such expression can result in a physiological effect. It is also understood that any of the expressed antibodies may be catalytic.

The present invention also provides for parts of the plants, particularly reproductive or storage parts, of the present invention. Plant parts, without limitation, include seed, endosperm, ovule and pollen. In a particularly preferred embodiment of the present invention, the plant part is a seed. In one embodiment the seed is a constituent of animal feed. In another embodiment, the plant part is constituent of human diet.

The present invention also provides a container of over 10,000, more preferably 20,000, and even more preferably 40,000 seeds where over 10%, more preferably 25%, more preferably 50% and even more preferably 75% or 90% of the seeds are seeds derived from a plant of the present invention.

The present invention also provides a container of over 10 kg, more preferably 25 kg, and even more preferably 50 kg seeds where over 10%, more preferably 25%, more preferably 50% and even more preferably 75% or 90% of the seeds are seeds derived from a plant of the present invention.

The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. Oil produced from a plant of the present invention can be admixed with one or more organic solvents or petroleum distillates.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). Selected, non-limiting approaches, for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new cultivars requires the development and selection of varieties, the crossing of these varieties and the selection of superior hybrid crosses. The hybrid seed can be produced by manual crosses between selected male-fertile parents or by using male sterility systems. Hybrids are selected for certain single gene traits such as pod color, flower color, seed yield, pubescence color, or herbicide resistance, which indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals from the best families is carried out. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seed of a population each generation of inbreeding.

Descriptions of other breeding methods that are commonly used for different traits and crops can be found in one of several reference books (e.g. Fehr, *Principles of Cultivar Development* Vol. 1, pp. 2–3 (1987)), the entirety of which is herein incorporated by reference).

The transgenic plants of the present invention may also be reproduced using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucellus, 2) diplospory where the embryo develops from an unreduced egg in an embryo sac derived from the megaspore mother cell, and 3) adventitious embryony where the embryo develops directly from a somatic cell. In most forms of apomixis, psuedogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636, which is herein incorporated by reference in its entirety.

(d) Other Organisms

A nucleic acid of the present invention may be introduced into any cell or organism such as a mammalian cell, mammal, fish cell, fish, bird cell, bird, algae cell, algae, fungal cell, fungi, or bacterial cell. A protein of the present invention may be produced in an appropriate cell or organism. Preferred hosts and transformants include: fungal cells such as *Aspergillus*, yeasts, mammals, particularly bovine and porcine, insects, bacteria and algae Methods to transform such cells or organisms are known in the art (EP 0 238 023; Yelton et al., *Proc. Natl. Acad. Sci* (U.S.A.), 81:1470–1474 (1984); Malardier et al., *Gene*, 78:147–156 (1989); Becker and Guarente, In: Abelson and Simon (eds.), *Guide to Yeast Genetics and Molecular Biology, Methods Enzymol.*, Vol. 194, pp. 182–187, Academic Press, Inc., New York; Ito et al., *J. Bacteriology*, 153:163 (1983); Hinnen et al., *Proc. Natl. Acad. Sci.* (*U.S.A.*), 75:1920 (1978); Bennett and LaSure (eds.), *More Gene Manipulations in Fungi*, Academic Press, CA (1991), all of which are herein incorporated by reference in their entirety). Methods to produce proteins of the present invention are also known (Kudla et al., *EMBO*, 9:1355–1364 (1990); Jarai and Buxton, *Current Genetics*, 26:2238–2244 (1994); Verdier, *Yeast*, 6:271–297 (1990); MacKenzie et al., *Journal of Gen. Microbiol.*, 139: 2295–2307 (1993); Hartl et al., *TIBS*, 19:20–25 (1994); Bergeron et al., *TIBS*, 19:124–128 (1994); Demolder et al., *J. Biotechnology*, 32:179–189 (1994); Craig, Science, 260: 1902–1903 (1993); Gething and Sambrook, *Nature*, 355: 3345 (1992); Puig and Gilbert, *J. Biol. Chem.*, 269:7764–7771 (1994); Wang and Tsou, *FASEB Journal*, 7:1515–1517 (9193); Robinson et al., *Bio/Technology*, 1:381–384 (1994); Enderlin and Ogrydziak, *Yeast*, 10:67–79 (1994); Fuller et al., *Proc. Natl. Acad. Sci.* (*U.S.A.*), 86:1434–1438 (1989); Julius et al., *Cell*, 37:1075–1089 (1984); Julius et al., *Cell*, 32:839–852 (1983), all of which are herein incorporated by reference in their entirety).

(e) Antibodies

One aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID Nos: 30, 31, 32, or 33. Such antibodies may be used to quantitatively or qualitatively detect the protein or peptide molecules of the invention. As used herein, an antibody or peptide is said to "specifically bind" to a protein or peptide molecule of the invention if such binding is not competitively inhibited by the presence of non-related molecules.

Nucleic acid molecules that encode all or part of the protein of the invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the invention may be expressed, via recombinant means, to yield proteins or peptides encoded by these nucleic acid molecules.

The antibodies that specifically bind proteins and protein fragments of the invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988), the entirety of which is herein incorporated by reference).

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the invention permits the identification of mimetic compounds derived from those molecules. These mimetic compounds may contain a fragment of the protein or peptide or merely a structurally similar region and nonetheless exhibits an ability to specifically bind to antibodies directed against that compound.

Exemplary Uses

Nucleic acid molecules and fragments thereof of the invention may be employed to obtain other nucleic acid molecules from the same species (nucleic acid molecules from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries. Methods for forming such libraries are well known in the art.

Nucleic acid molecules and fragments thereof of the invention may also be employed to obtain nucleic acid homologs. Such homologs include the nucleic acid molecule of other plants or other organisms (e.g., alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus*, etc.) including the nucleic acid molecules that encode, in whole or in part, protein homologs of other plant species or other organisms, sequences of genetic elements, such as promoters and transcriptional regulatory elements. Particularly preferred plants are selected from the group consisting of maize, canola, soybean, *crambe*, mustard, castor bean, peanut, sesame, cottonseed, linseed, safflower, oil palm, flax and sunflower.

Such molecules can be readily obtained by using the above-described nucleic acid molecules or fragments thereof to screen cDNA or genomic libraries obtained from such plant species. Methods for forming such libraries are well known in the art. Such homolog molecules may differ in their nucleotide sequences from those found in one or more of SEQ ID NOs: 1–4, 6–29 or complements thereof because complete complementarity is not needed for stable hybridization. The nucleic acid molecules of the invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143–4146 (1986); Goodchild et al., *Proc. Natl. Acad. Sci.* (*U.S.A.*) 85:5507–5511 (1988); Wickstrom et al., *Proc. Natl. Acad. Sci.* (*U.S.A.*) 85:1028–1032 (1988); Holt et al, *Molec. Cell. Biol.* 8:963–973 (1988); Gerwirtz et al., *Science* 242:1303–1306 (1988); Anfossi et al., *Proc. Natl. Acad. Sci.* (*U.S.A.*) 86:3379–3383 (1989); Becker et al., *EMBO J.* 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263–273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

Promoter sequences and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating nucleic acid molecules of the present invention with members of genomic libraries and recovering clones that hybridize to such nucleic acid molecules thereof. In a second embodiment, methods of "chromosome walking," or inverse PCR may be used to obtain such sequences (Frohman et al., *Proc. Natl. Acad. Sci.* (*U.S.A.*) 85:8998–9002 (1988); Ohara et al., *Proc. Natl. Acad. Sci.* (*U.S.A.*) 86:5673–5677 (1989); Pang et al., *Biotechniques* 22:1046–1048 (1977); Huang et al., *Methods Mol. Biol.* 69:89–96 (1997); Huang et al., *Method Mol. Biol.* 67:287–294 (1997); Benkel et al., *Genet. Anal.* 13:123–127 (1996); Hartl et al., *Methods Mol. Biol.* 58:293–301 (1996)). The term "chromosome walking" means a process of extending a genetic map by successive hybridization steps.

The nucleic acid molecules of the invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y.). Promoters obtained utilizing the nucleic acid molecules of the invention could also be modified to affect their control characteristics. Examples of such modifications would include but are not limited to enhancer sequences. Such genetic elements could be used to enhance gene expression of new and existing traits for crop improvement.

Another subset of the nucleic acid molecules of the invention includes nucleic acid molecules that are markers. The markers can be used in a number of conventional ways in the field of molecular genetics. Such markers include nucleic acid molecules SEQ ID NOs: 1–4, 6–29 or complements thereof or fragments of either that can act as markers and other nucleic acid molecules of the present invention that can act as markers. Genetic markers of the invention include "dominant" or "codominant" markers. "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is in either the homozygous or heterozygous condition. The absence of the dominant marker phenotype (e.g., absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

The genomes of animals and plants naturally undergo spontaneous mutation in the course of their continuing evolution (Gusella, *Ann. Rev. Biochem.* 55:831–854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113–115 (1992); Jones et al., *Eur. J. Haematol.* 39:144–147 (1987); Horn et al., PCT Patent Application WO91/14003; Jeffreys, European Patent Application 370,719; Jeffreys, U.S. Pat. No. 5,175,082; Jeffreys et al., *Amer. J. Hum. Genet.* 39:11–24 (1986); Jeffreys et al., *Nature* 316:76–79 (1985); Gray et al., *Proc. R. Acad. Soc. Lond.* 243:241–253 (1991); Moore et al., *Genomics* 10:654–660 (1991); Jeffreys et al., *Anim. Genet.* 18:1–15 (1987); Hillel et al., *Anim. Genet.* 20:145–155 (1989); Hillel et al., *Genet.* 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, organisms that possess a variant sequence can be distinguished from those having the original sequence by restriction fragment analysis. Polymorphisms that can be identified in this manner are termed "restriction fragment length polymorphisms" ("RFLPs") (Glassberg, UK Patent Application 2135774; Skolnick et al., *Cytogen. Cell Genet.* 32:58–67 (1982); Botstein et al., *Ann. J. Hum. Genet.* 32:314–331 (1980); Fischer et al., (PCT Application WO90/13668; Uhlen, PCT Application WO90/11369).

Polymorphisms can also be identified by Single Strand Conformation Polymorphism (SSCP) analysis (Elles, *Methods in Molecular Medicine: Molecular Diagnosis of Genetic Diseases*, Humana Press (1996)); Orita et al., *Genomics* 5: 874–879 (1989)). A number of protocols have been described for SSCP including, but not limited to, Lee et al., *Anal. Biochem.* 205:289–293 (1992); Suzuki et al., *Anal. Biochem.* 192:82–84 (1991); Lo et al., *Nucleic Acids Research* 20.1005–1009 (1992); Sarkar et al., *Genomics* 13.441443 (1992). It is understood that one or more of the nucleic acids of the invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407–4414 (1995)). This method allows for the specific co-amplification of high numbers of restriction fragments, which can be visualized by PCR without knowledge of the nucleic acid sequence. It is understood that one or more of the nucleic acids of the invention may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531–6535 (1990)) and cleaveable amplified polymorphic sequences (CAPS) (Lyamichev et al., *Science* 260: 778–783 (1993)). It is understood that one or more of the nucleic acid molecules of the invention, may be utilized as markers or probes to detect polymorphisms by RAPD or CAPS analysis.

Single Nucleotide Polymorphisms (SNPs) generally occur at greater frequency than other polymorphic markers and are spaced with a greater uniformity throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a result of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314–331 (1980), the entirety of which is herein incorporated reference; Konieczny and Ausubel, *Plant J.* 4:403–410 (1993), the entirety of which is herein incorporated by reference), enzymatic and chemical mismatch assays (Myers et al., *Nature* 313:495498 (1985), the entirety of which is herein incorporated by reference), allele-specific PCR (Newton et al., *Nucl. Acids Res.* 17:2503–2516 (1989), the entirety of which is herein incorporated by reference; Wu et al., *Proc. Natl. Acad. Sci. USA* 86:2757–2760 (1989), the entirety of which is herein incorporated by reference), ligase chain reaction (Barany, *Proc. Natl. Acad. Sci. USA* 88:189–193 (1991), the entirety of which is herein incorporated by reference), single-strand conformation polymorphism analysis (Labrune et al., *Am. J. Hum. Genet.* 48: 1115–1120 (1991), the entirety of which is herein incorporated by reference), single base primer extension (Kuppuswamy et al., *Proc. Natl. Acad. Sci. USA* 88:1143–1147 (1991), Goelet U.S. Pat. No. 6,004,744; Goelet U.S. Pat. No. 5,888,819; all of which are herein incorporated by reference in their entirety), solid-phase ELISA-based oligonucleotide ligation assays (Nikiforov et al., *Nucl. Acids Res.* 22:41674175 (1994), dideoxy fingerprinting (Sarkar et al., *Genomics* 13:441443 (1992), the entirety of which is herein incorporated by reference), oligonucleotide fluorescence-quenching assays (Livak et al., *PCR Methods Appl.* 4:357–362 (1995a), the entirety of which is herein incorporated by reference), 5'-nuclease allele-specific hybridization TaqMan™ assay (Livak et al., *Nature Genet.* 9:341–342 (1995), the entirety of which is herein incorporated by reference), template-directed dye-terminator incorporation (TDI) assay (Chen and Kwok, *Nucl. Acids Res.* 25:347–353 (1997), the entirety of which is herein incorporated by reference), allele-specific molecular beacon assay (Tyagi et al., *Nature Biotech.* 16: 49–53 (1998), the entirety of which is herein incorporated by reference), PinPoint assay (Haff and Smirnov, *Genome Res.* 7: 378–388 (1997), the entirety of which is herein incorporated by reference), dCAPS analysis (Neff et al, *Plant J.* 14:387–392 (1998), the entirety of which is herein incorporated by reference), pyrosequencing (Ronaghi et al, *Analytical Biochemistry* 267:65–71 (1999); Ronaghi et al PCT application WO 98/13523; Nyren et al PCT application WO 98/28440, all of which are herein incorporated by reference in their entirety; http//www.pyrosequencing.com), using mass spectrometry, e.g. the Masscode™ system (Howbert et al WO 99/05319; Howber et al WO 97127331, all of which are herein incorporated by reference in their entirety; http//www.rapigene.com; Becker et al PCT application WO 98/26095; Becker et al PCT application; WO 98/12355; Becker et al PCT application WO 97/33000; Monforte et al U.S. Pat. No. 5,965,363, all of which are herein incorporated by reference in their entirety), invasive cleavage of oligonucleotide probes (Lyamichev et al *Nature Biotechnology* 17:292–296, herein incorporated by reference in its entirety; http//www.twt.com), and using high density oligonucleotide arrays (Hacia et al *Nature Genetics* 22:164–167; herein incorporated by reference in its entirety; http//www.affymetrix.com).

Polymorphisms may also be detected using allele-specific oligonucleotides (ASO), which, can be for example, used in combination with hybridization based technology including southern, northern, and dot blot hybridizations, reverse dot blot hybridizations and hybridizations performed on microarray and related technology.

The stringency of hybridization for polymorphism detection is highly dependent upon a variety of factors, including length of the allele-specific oligonucleotide, sequence composition, degree of complementarity (i.e. presence or absence of base mismatches), concentration of salts and other factors such as formamide, and temperature. These factors are important both during the hybridization itself and during subsequent washes performed to remove target polynucleotide that is not specifically hybridized. In practice, the conditions of the final, most stringent wash are most critical. In addition, the amount of target polynucleotide that is able to hybridize to the allele-specific oligonucleotide is also governed by such factors as the concentration of both the ASO and the target polynucleotide, the presence and concentration of factors that act to "tie up" water molecules, so as to effectively concentrate the reagents (e.g., PEG, dextran, dextran sulfate, etc.), whether the nucleic acids are immobilized or in solution, and the duration of hybridization and washing steps.

Hybridizations are preferably performed below the melting temperature ($T_m$) of the ASO. The closer the hybridization and/or washing step is to the $T_m$, the higher the stringency. $T_m$ for an oligonucleotide may be approximated, for example, according to the following formula: $T_m=81.5+16.6\times(\log 10[Na+])+0.41\times(\% G+C)-675/n$; where [Na+] is the molar salt concentration of Na+ or any other suitable cation and n=number of bases in the oligonucleotide. Other formulas for approximating $T_m$ are available and are known to those of ordinary skill in the art.

Stringency is preferably adjusted so as to allow a given ASO to differentially hybridize to a target polynucleotide of the correct allele and a target polynucleotide of the incorrect allele. Preferably, there will be at least a two-fold differential between the signal produced by the ASO hybridizing to a target polynucleotide of the correct allele and the level of the signal produced by the ASO cross-hybridizing to a target polynucleotide of the incorrect allele (e.g., an ASO specific for a mutant allele cross-hybridizing to a wild-type allele). In more preferred embodiments of the present invention, there is at least a five-fold signal differential. In highly preferred embodiments of the present invention, there is at least an order of magnitude signal differential between the ASO hybridizing to a target polynucleotide of the correct allele and the level of the signal produced by the ASO cross-hybridizing to a target polynucleotide of the incorrect allele.

While certain methods for detecting polymorphisms are described herein, other detection methodologies may be utilized. For example, additional methodologies are known and set forth, in Birren et al., *Genome Analysis,* 4:135–186, *A Laboratory Manual. Mapping Genomes,* Cold Spring Harbor Laboratory Press, Cold Spring Harbor, N.Y. (1999); Maliga et al., *Methods in Plant Molecular Biology. A Laboratory Course Manual,* Cold Spring Harbor Laboratory Press, Cold Spring Harbor, N.Y. (1995); Paterson, *Biotechnology Intelligence Unit: Genome Mapping in Plants,* R.G. Landes Co., Georgetown, Tex., and Academic Press, San Diego, Calif. (1996); *The Maize Handbook,* Freeling and Walbot, eds., Springer-Verlag, New York, N.Y. (1994); *Methods in Molecular Medicine: Molecular Diagnosis of Genetic Diseases,* Elles, ed., Humana Press, Totowa, N.J. (1996); Clark, ed., *Plant Molecular Biology: A Laboratory Manual,* Clark, ed., Springer-Verlag, Berlin, Germany (1997), all of which are herein incorporated by reference in their entirety.

Requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185–199 (1989) and the interval mapping, based on maximum likelihood methods described by Lander and Botstein, *Genetics* 121:185–199 (1989) and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$(MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185–199 (1989) and further described by Arús and Moreno-González, *Plant Breeding,* Hayward et al., (eds.) Chapman & Hall, London, pp. 314–331 (1993).

In a preferred embodiment of the present invention the nucleic acid marker exhibits a LOD score of greater than 2.0, more preferably 2.5, even more preferably greater than 3.0 or 4.0 with the trait or phenotype of interest. In a preferred embodiment, the trait of interest is altered, preferably increased phytosterol levels or compositions.

Additional models can be used. Many modifications and alternative approaches to interval mapping have been reported, including the use non-parametric methods (Kruglyak and Lander, *Genetics* 139:1421–1428 (1995)). Multiple regression methods or models can be also be used, in which the trait is regressed on a large number of markers (Jansen, *Biometrics in Plant Breeding,* van Oijen and Jansen (eds.), Proceedings of the Ninth Meeting of the Eucarpia Section Biometrics in Plant Breeding, The Netherlands, pp. 116–124 (1994); Weber and Wricke, *Advances in Plant Breeding,* Blackwell, Berlin, 16 (1994)). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447–1455 (1994), and Zeng, *Genetics* 136:1457–1468 (1994). Generally, the use of cofactors reduces the bias and sampling error of the estimated QTL positions (Utz and Melchinger, *Biometrics in Plant Breeding,* van Oijen and Jansen (eds.) Proceedings of the Ninth Meeting of the Eucarpia Section Biometrics in Plant Breeding, The Netherlands, pp. 195–204 (1994), thereby improving the precision and efficiency of QTL mapping (Zeng, *Genetics* 136:1457–1468 (1994), herein incorporated by reference in its entirety). These models can be extended to multi-environment experiments to analyze genotype-environment interactions (Jansen et al., *Theo. Appl. Genet.* 91:33–37 (1995), herein incorporated by reference in its entirety).

It is understood that one or more of the nucleic acid molecules of the invention may be used as molecular markers. It is also understood that one or more of the protein molecules of the invention may be used as molecular markers.

In a preferred embodiment, the polymorphism is present and screened for in a mapping population, e.g. a collection of plants capable of being used with markers such as polymorphic markers to map genetic position of traits. The choice of appropriate mapping population often depends on the type of marker systems employed (Tanksley et al., J. P. Gustafson and R. Appels (eds.). Plenum Press, New York, pp. 157–173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large number of polymorphisms when compared to progeny in a narrow cross (adapted×adapted).

An $F_2$ population is the first generation of selfing (self-pollinating) after the hybrid seed is produced. Usually a single $F_1$ plant is selfed to generate a population segregating for all the genes in Mendelian (1:2:1) pattern. Maximum genetic information is obtained from a completely classified $F_2$ population using a codominant marker system (Mather, Measurement of linkage in Heredity: Methuen and Co., (1938), the entirety of which is herein incorporated by reference). In the case of dominant markers, progeny tests (e.g., $F_3$, $BCF_2$) are required to identify the heterozygotes, in order to classify the population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations e.g. $F_3$ or $BCF_2$ can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter. *Proc. Natl. Acad. Sci.* (*U.S.A.*) 89:1477–1481 (1992), the entirety of which is herein incorporated by reference). However, as the distance between markers becomes larger (ie., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477–1481 (1992), the entirety of which is herein incorporated by reference). Information obtained from backcross populations using either codominant or dominant markers is less than that obtained from $F_2$ populations because one, rather than two, recombinant gamete is sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) (created by many backcrosses to produce a collection of individuals that is nearly identical in genetic composition except for the trait or genomic region under interrogation) can be used as a mapping population. In mapping with NILs, only a portion of the polymorphic loci is expected to map to a selected region.

Bulk segregant analysis (BSA) is a method developed for the rapid identification of linkage between markers and traits of interest (Michelmore et al., *Proc. Natl. Acad. Sci. U.S.A.* 88:9828–9832 (1991), the entirety of which is herein incorporated by reference). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

In an aspect of the present invention, one or more of the nucleic molecules of the present invention are used to determine the level (i.e., the concentration of mRNA in a sample, etc.) in a plant (preferably maize, canola, soybean, *crambe*, mustard, castor bean, peanut, sesame, cottonseed, linseed, safflower, oil palm, flax or sunflower) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue).

As used herein, the Expression Response manifested by a cell or tissue is said to be "altered" if it differs from the Expression Response of cells or tissues of plants not exhibiting the phenotype. To determine whether a Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present).

Alternatively, the assay may be conducted as a qualitative assay that indicates either that the mRNA is present, or that its level exceeds a user set, predefined value.

A number of methods can be used to compare the expression response between two or more samples of cells or tissue. These methods include hybridization assays, such as northerns, RNAse protection assays, and in situ hybridization. Alternatively, the methods include PCR-type assays. In a preferred method, the expression response is compared by hybridizing nucleic acids from the two or more samples to an array of nucleic acids. The array contains a plurality of suspected sequences known or suspected of being present in the cells or tissue of the samples.

An advantage of in situ hybridization over more conventional techniques for the detection of nucleic acids is that it allows an investigator to determine the precise spatial population (Angerer et al., *Dev. Biol.* 101:477–484 (1984); Angerer et al., *Dev. Biol.* 112:157–166 (1985); Dixon et al., *EMBO J.* 10:1317–1324 (1991)). In situ hybridization may be used to measure the steady-state level of RNA accumulation (Hardin et al., *J. Mol. Biol.* 202:417431 (1989)). A number of protocols have been devised for in situ hybridization, each with tissue preparation, hybridization and washing conditions (Meyerowitz, *Plant Mol. Biol. Rep.* 5:242–250 (1987); Cox and Goldberg, In: *Plant Molecular Biology: A Practical Approach*, Shaw (ed.), pp. 1–35, IRL Press, Oxford (1988); Raikhel et al., *In situ RNA hybridization in plant tissues*, In: *Plant Molecular Biology Manual*, vol. B9: 1–32, Kluwer Academic Publisher, Dordrecht, Belgium (1989)).

In situ hybridization also allows for the localization of proteins within a tissue or cell (Wilkinson, *In Situ Hybridization*, Oxford University Press, Oxford (1992); Langdale, *In Situ hybridization* In: *The Maize Handbook*, Freeling and Walbot (eds.), pp. 165–179, Springer-Verlag, New York (1994)). It is understood that one or more of the molecules of the invention, preferably one or more of the nucleic acid molecules or fragments thereof of the invention or one or more of the antibodies of the invention may be utilized to detect the level or pattern of a protein or mRNA thereof by in situ hybridization.

Fluorescent in situ hybridization allows the localization of a particular DNA sequence along a chromosome, which is useful, among other uses, for gene mapping, following chromosomes in hybrid lines, or detecting chromosomes with translocations, transversions or deletions. In situ hybridization has been used to identify chromosomes in several plant species (Griffor et al., *Plant Mol. Biol.* 17:101–109 (1991); Gustafson et al., *Proc. Natl. Acad. Sci.* (*U.S.A.*) 87:1899–1902 (1990); Mukai and Gill, *Genome* 34:448452 (1991); Schwarzacher and Heslop-Harrison, *Genome* 34:317–323 (1991); Wang et al., *Jpn. J. Genet.* 66:313–316 (1991); Parra and Windle, *Nature Genetics* 5:17–21 (1993)). It is understood that the nucleic acid molecules of the invention may be used as probes or markers to localize sequences along a chromosome.

Another method to localize the expression of a molecule is tissue printing. Tissue printing provides a way to screen, at the same time on the same membrane many tissue sections from different plants or different developmental stages (Yomo and Taylor, *Planta* 112:3543 (1973); Harris and Chrispeels, *Plant Physiol.* 56:292–299 (1975); Cassab and Varner, *J. Cell Biol.* 105:2581–2588 (1987); Spruce et al., *Phytochemistry* 26:2901–2903 (1987); Barres et al., *Neuron* 5:527–544 (1990); Reid and Pont-Lezica, *Tissue Printing: Tools for the Study of Anatomy, Histochemistry and Gene Expression*, Academic Press, New York, N.Y. (1992); Reid et al., *Plant Physiol.* 93:160–165 (1990); Ye et al., *Plant J.* 1:175–183 (1991)).

One skilled in the art can refer to general reference texts for detailed descriptions of known techniques discussed herein or equivalent techniques. These texts include *Current Protocols in Molecular Biology* Ausubel, et al., eds., John Wiley & Sons, N.Y. (1989), and supplements through September (1998), *Molecular Cloning, A Laboratory Manual*, Sambrook et al, $2^{nd}$ Ed., Cold Spring Harbor Press, Cold Spring Harbor, N.Y. (1989), *Genome Analysis: A Laboratory Manual 1: Analyzing DNA*, Birren et al., Cold Spring Harbor Press, Cold Spring Harbor, N.Y. (1997); *Genome Analysis: A Laboratory Manual 2: Detecting Genes*, Birren et al., Cold Spring Harbor Press, Cold Spring Harbor, N.Y. (1998); *Genome Analysis: A Laboratory Manual 3: Cloning Systems*, Birren et al., Cold Spring Harbor Press, Cold Spring Harbor, N.Y. (1999); *Genome Analysis: A Laboratory Manual 4: Mapping Genomes*, Birren et al., Cold Spring Harbor Press, Cold Spring Harbor, N.Y. (1999); *Plant Molecular Biology: A Laboratory Manual*, Clark, Springer-Verlag, Berlin, (1997), *Methods in Plant Molecular Biology*, Maliga et al., Cold Spring Harbor Press, Cold Spring Harbor, N.Y. (1995). These texts can, of course, also be referred to in making or using an aspect of the invention. It is understood that any of the agents of the invention can be substantially purified and/or be biologically active and/or recombinant.

Having now generally described the invention, the same will be more readily understood through reference to the following examples which are provided by way of illustration, and are not intended to be limiting of the present invention, unless specified.

EXAMPLE 1

Identification of Yeast HES1

The yeast strain LPY9 (MATa, leu2, Ura3, his3) is grown overnight and inoculated into SD+ hul (histidine, uracil, leucine) media. Aliquots of the culture are treated with ketoconazole (an inhibitor of C-14α demethylase ($P450_{14DM}$) enzyme) at 10 ug/ml, 50 ug/ml, and 10 ug/ml, corresponding to 10 ppm, 50 ppm, and 100 ppm, respectively. A sample of each is collected at 2, 4, and 6 hours after treatment. Control samples treated with DMSO (dimethyl sulfoxide-solvent for ketoconazole) but not with ketoconazole are also collected. Total RNA from each sample is collected by conventional methods, such as a Zirconium/Silica bead binding and extraction method. The sequence content of each sample is analyzed and compared by hybridizing each of them to a number of yeast ORF sequences immobilized on a Nylon membrane in an array format.

A similar comparison of a wild type yeast strain and a double mutant strain is made. The double mutant CJ517 (MATa, erg11::URA3, erg3::LEU2, leu2, ura3, his4) [erg11, erg3 double mutant] is compared to LPY9 after growth in both YPD and SD+hul media. Samples are collected at approximately 0, 2, 4, and 6 hours after inoculation.

Using this method, over 600 RNA transcripts levels are shown to be altered. A yeast transcript that encodes HES1 is identified as a transcript that is particularly effected by the addition of ketoconazole (SEQ ID NO: 5)(Table 1).

TABLE 1*

| Seq. Num. | Clone ID | ALIAS | CJ-4 hr/ LP-4 hr | K-50/CK | K-100/CK | Gene Description |
|---|---|---|---|---|---|---|
| 5 | YOR237W | (HES1) | 134.648161 | 1417.6262 | 1358.1235 | Protein implicated in ergosterol biosynthesis, member of the KES1/HES1/OSH1/YKR003W family of oxysterol-binding (OSBP) proteins |

*Table Headings:
Clone ID: A clone ID designation number;
Alias: Alternative gene names used in the literature. This information is provided by YPD™, Hodges et al. Nucl. Acids Res. 27:69–73 (1999), the entirety of which is herein incorporated by reference;
CJ-4 hr/LP-4 hr: Expression level in the mutant CJ517 as compared with the respective wild type strain LPY9 at 4 hr sampling of log phase growth of yeast (ratio of mutant expression level/control expression level). CJ refers to the mutant CJ517 (The mutant is defective in the gene (ERG11) codes for C14 demethylase enzyme in the sterol biosynthetic pathway). LP refers to the respective wild type strain LPY9, used to compare the gene expression profile with the mutant;
K-50/CK: Expression level in the wild type yeast LPY9, at 2 hr after treatment with 50 micro gram/ml ketoconazole as compared to the wild type LPY9 strain without ketoconazole treatment (ratio of treatment expression level/control expression level). K refers to ketoconazole treatment;
K-100/CK: Expression level in the wild type yeast LPY9, at 2 hr after treatment with 100 micro gram/ml ketoconazole as compared to the wild type LPY9 strain without ketoconazole treatment (ratio of treatment expression level/control expression level);
Gene Description: Description of the clone listed in column 1.

EXAMPLE 2

Sequences that encode for the yeast HES1 protein are used to search databases for homologues from other species. A number of different databases can be used for these searches, including, for example, dbEST, GenBank, EMBL, SwissProt, PIR, and GENES. In addition, various algorithms for searching can be selected, such as, for example, the BLAST suite of programs at the default values. Typically, matches found with BLAST P values equal or less than 0.001 (probability) or BLAST Score of equal or greater than 90 are classified as hits. If the program is used to determine the hit is HMMSW then the score refers to HMMSW score. The GenBank database is searched with BLASTN and BLASTX (default values) using sequences as series. Sequences that pass the hit probability threshold of $10\ e^{-8}$ are considered hits.

TABLE 2

| Seq. Num. | Clone ID | Sequence: DNA/Protein | Hit description | Species |
|---|---|---|---|---|
| 1 | 701100307CPR9855 | DNA | Yeast HES 1 homolog | soybean |
| 2 | 701001443CPR9857 | DNA | Yeast HES 1 homolog | soybean |
| 3 | 701010572CPR9854 | DNA | Yeast HES 1 homolog | soybean |
| 4 | 701176735CPR9736 | DNA | Yeast HES 1 homolog | maize |
| 5 | Z75145 | DNA | Protein implicated in ergosterol biosynthesis, member of the KES1/HES1/OSH1/YKR003W family of oxysterol-binding (OSBP) proteins | yeast |
| 30 | 701100307CPR9855 | Protein | Yeast HES 1 homolog | soybean |
| 31 | 701001443CPR9857 | Protein | Yeast HES 1 homolog | soybean |
| 32 | 701010572CPR9854 | Protein | Yeast HES 1 homolog | soybean |
| 33 | 701176735CPR9736 | Protein | Yeast HES 1 homolog | maize |
| 34 | Z75145 | Protein | Protein implicated in ergosterol biosynthesis, member of the KES1/HES1/OSH1/YKR003W family of oxysterol-binding (OSBP) proteins | yeast |
| 6 | 701003888H1 | DNA | Yeast HES 1 homolog | soybean |
| 7 | 701001351H1 | DNA | Yeast HES 1 homolog | soybean |
| 8 | 700672545H1 | DNA | Yeast HES 1 homolog | soybean |
| 9 | 700664054H1 | DNA | Yeast HES 1 homolog | soybean |
| 10 | 700665644H1 | DNA | Yeast HES 1 homolog | soybean |
| 11 | 700764248H1 | DNA | Yeast HES 1 homolog | soybean |
| 12 | 700851444H1 | DNA | Yeast HES 1 homolog | soybean |
| 13 | 700971910H1 | DNA | Yeast HES 1 homolog | soybean |
| 14 | 700652932H1 | DNA | Yeast HES 1 homolog | soybean |
| 15 | 700982894H1 | DNA | Yeast HES 1 homolog | soybean |
| 16 | 701120140H1 | DNA | Yeast HES 1 homolog | soybean |
| 17 | 701064234H1 | DNA | Yeast HES 1 homolog | soybean |
| 18 | 700954013H1 | DNA | Yeast HES 1 homolog | soybean |
| 19 | 701129375H1 | DNA | Yeast HES 1 homolog | soybean |
| 20 | 701043941H1 | DNA | Yeast HES 1 homolog | soybean |
| 21 | LIB24-114-Q1-E1-H8 | DNA | Arabidopsis HES 1 homolog | A. thaliana |
| 22 | LIB22-016-Q1-E1-F3 | DNA | Arabidopsis HES 1 homolog | A. thaliana |
| 23 | LIB25-101-Q1-E1-F1 | DNA | Arabidopsis HES 1 homolog | A. thaliana |
| 24 | AA042357 | DNA | Arabidopsis HES 1 homolog | A. thaliana |
| 25 | AA720163 | DNA | Arabidopsis HES 1 homolog | A. thaliana |

TABLE 2-continued

| Seq. Num. | Clone ID | Sequence: DNA/Protein | Hit description | Species |
|---|---|---|---|---|
| 26 | Z29936 | DNA | Arabidopsis HES 1 homolog | *A. thaliana* |
| 27 | T76850 | DNA | Arabidopsis HES 1 homolog | *A. thaliana* |
| 28 | T76580 | DNA | Arabidopsis HES 1 homolog | *A. thaliana* |
| 29 | AA586043 | DNA | Arabidopsis HES 1 homolog | *A. thaliana* |

What is claimed is:

1. A substantially purified nucleic acid molecule that encodes a protein comprising the amino acid sequence of SEQ ID NO: 33.

2. The substantially purified nucleic acid molecule of claim 1, wherein the nucleic acid molecule comprises the nucleic acid sequence of SEQ ID NO: 4.

3. A plant having a nucleic acid molecule which comprises: (A) a promoter region which functions in a plant cell to cause the production of a mRNA molecule; (B) an exogenous structural nucleic acid molecule encoding a protein or fragment thereof comprising SEQ ID NO: 33, and (C) a 3' non-translated sequence that functions in the plant cell to cause termination of transcription and addition of polyadenylated ribonucleotides to a 3' end of the mRNA molecule.

4. The plant according to claim 3, wherein said plant is selected from the group consisting of maize, canola, soybean, *crambe*, mustard, castor bean, peanut, sesame, cottonseed, linseed, safflower, oil palm, flax, *Cuphea*, rapeseed, and sunflower.

5. The plant according to claim 3, wherein said plant exhibits increased phytosterol levels relative to a plant with a similar genetic background but lacking said exogenous structural nucleic acid molecule.

6. A method of producing a plant containing an expressed protein in a plant comprising: (A) transforming the plant with a functional nucleic acid molecule, wherein the functional nucleic acid molecule comprises a promoter region, wherein the promoter region is linked to a structural region, wherein the structural region comprises a nucleic acid sequence that encodes a protein comprising an amino acid sequence of SEQ ID NO: 33, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

7. The method of producing a plant according to claim 6, wherein said plant is selected from the group consisting of maize, canola, soybean, *crambe*, mustard, castor bean, peanut, sesame, cottonseed, linseed, safflower, oil palm, flax and sunflower.

8. The method of producing a plant according to claim 6, wherein said plant exhibits increased phytosterol levels relative to a plant with a similar genetic background but lacking said exogenous structural nucleic acid molecule.

* * * * *

SEQUENCE LISTING

<160> NUMBER OF SEQ ID NOS: 34

<210> SEQ ID NO 1
<211> LENGTH: 1358
<212> TYPE: DNA
<213> ORGANISM: Glycine max
<220> FEATURE:
<221> NAME/KEY: CDS
<222> LOCATION: (24)...(1100)

<400> SEQUENCE: 1

```
gaattcggct cgagtttgaa cca atg aca atg ctt cag aaa atg gct gag ctt       53
                         Met Thr Met Leu Gln Lys Met Ala Glu Leu
                          1               5                  10 atg gag tac tct tac ctg tta gat atg gcg gac aag act gag gat cca      101
Met Glu Tyr Ser Tyr Leu Leu Asp Met Ala Asp Lys Thr Glu Asp Pro
             15                  20                  25 tac atg aga cta gta tat gct tca tca ttc ttt ata tct gtc tac tat      149
Tyr Met Arg Leu Val Tyr Ala Ser Ser Phe Phe Ile Ser Val Tyr Tyr
         30                  35                  40 gcc tat caa cga acg tgg aag cca ttc aat cca att ctt ggt gag act      197
Ala Tyr Gln Arg Thr Trp Lys Pro Phe Asn Pro Ile Leu Gly Glu Thr
     45                  50                  55 tat gaa atg gtt aac cat ggt ggc att aca ttt ata tca gag cag gtc      245
Tyr Glu Met Val Asn His Gly Gly Ile Thr Phe Ile Ser Glu Gln Val
 60                  65                  70 agt cat cac cct cca atg agt gct ggg cat gct gaa act gaa cat ttc      293
Ser His His Pro Pro Met Ser Ala Gly His Ala Glu Thr Glu His Phe
 75                  80                  85                  90 act tat gat gtt aca tca aaa ttg aaa acc aaa ttt ctc ggc aac tca      341
Thr Tyr Asp Val Thr Ser Lys Leu Lys Thr Lys Phe Leu Gly Asn Ser
             95                 100                 105 gtt gat gta tat cct gtt gga aga acg cgt gtt acc ctc aaa aga gat      389
Val Asp Val Tyr Pro Val Gly Arg Thr Arg Val Thr Leu Lys Arg Asp
         110                 115                 120 ggt gtg gtc ctt gat ttg gtg cct cct cct aca aaa gtt agc aac ttg      437
Gly Val Val Leu Asp Leu Val Pro Pro Pro Thr Lys Val Ser Asn Leu
     125                 130                 135 att ttt gga cga act tgg att gat tca cca gga gag atg atc ctg aca      485
Ile Phe Gly Arg Thr Trp Ile Asp Ser Pro Gly Glu Met Ile Leu Thr
 140                 145                 150 aat ctg act aca ggg gac aaa gtg gtg ctg tat ttt caa cca tgt ggc      533
Asn Leu Thr Thr Gly Asp Lys Val Val Leu Tyr Phe Gln Pro Cys Gly
155                 160                 165                 170 tgg ttt gga tat gaa gtg gat ggg tac gtg tat aat tct gct gac gag      581
Trp Phe Gly Tyr Glu Val Asp Gly Tyr Val Tyr Asn Ser Ala Asp Glu
             175                 180                 185 cct aag ata ctg atg act gga aaa tgg aat gag gct atg aat tat caa      629
Pro Lys Ile Leu Met Thr Gly Lys Trp Asn Glu Ala Met Asn Tyr Gln
         190                 195                 200
```

```
gtt tgt gac tca gag gga gaa cca ctt cca ggc act gag ttg aaa gag      677
Val Cys Asp Ser Glu Gly Glu Pro Leu Pro Gly Thr Glu Leu Lys Glu
        205                 210                 215 att tgg aga gtt gct gat acc ccg aag aag gac aag ttc cag tac acg      725
Ile Trp Arg Val Ala Asp Thr Pro Lys Lys Asp Lys Phe Gln Tyr Thr
220                 225                 230 cat ttt gca cac aag att aac agc ttt gac act gct ccc aag aag ttg      773
His Phe Ala His Lys Ile Asn Ser Phe Asp Thr Ala Pro Lys Lys Leu
235                 240                 245                 250 ttg gca tct gac tct cgt cta cgt cct gat aga atg gcc ctt gag aag      821
Leu Ala Ser Asp Ser Arg Leu Arg Pro Asp Arg Met Ala Leu Glu Lys
        255                 260                 265 ggt gac cta tcc aca tct ggt tat gag aag agc agt ttg gag gag agg      869
Gly Asp Leu Ser Thr Ser Gly Tyr Glu Lys Ser Ser Leu Glu Glu Arg
        270                 275                 280 caa aga gct gag aag aga aac cga gag gcc aag ggc cat aag ttc act      917
Gln Arg Ala Glu Lys Arg Asn Arg Glu Ala Lys Gly His Lys Phe Thr
        285                 290                 295 cct aga tgg ttt gat tta aca gat gaa gta act cct acc cct tgg ggt      965
Pro Arg Trp Phe Asp Leu Thr Asp Glu Val Thr Pro Thr Pro Trp Gly
300                 305                 310 gac ttg gaa gtt tac caa tac aac ggt aaa tat acc caa cat tgt gct     1013
Asp Leu Glu Val Tyr Gln Tyr Asn Gly Lys Tyr Thr Gln His Cys Ala
315                 320                 325                 330 gcc gtt gat agt tct gag tgc att gaa gtg cct gac atc aga cca gaa     1061
Ala Val Asp Ser Ser Glu Cys Ile Glu Val Pro Asp Ile Arg Pro Glu
                335                 340                 345 ttc aac cct tgg caa tat gat aat ttg gat gct gaa tag tgagcatcct     1110
Phe Asn Pro Trp Gln Tyr Asp Asn Leu Asp Ala Glu
        350                 355 tgtggaattc tttctatttt ttttaaatat cattttgtta ttaagtttgt aatgtaatct   1170
tgattggaat gcttgaaatt tggttttgtt tttgggttgt tttatcactg tagtatttga   1230
ttaattaata gtagctatgt tagttcatca gttcactttg catggataaa tgctagtagg   1290
gaaattaaag ttatcttcca aaaaaaaaaa aaaaaaaaa aaaaaaaaa aaaaagggc     1350 ggccgccg                                                            1358

<210> SEQ ID NO 2
<211> LENGTH: 1136
<212> TYPE: DNA
<213> ORGANISM: Glycine max
<220> FEATURE:
<221> NAME/KEY: CDS
<222> LOCATION: (73)...(975)

<400> SEQUENCE: 2
gaattcggct cgaggtcaca acttcagtgc tatggtgaat cagtgtattg cacaggttcg     60
gacttgctaa gc atg tgc aac aat ggt cag agt cca ctt gat agg ttc ata    111
              Met Cys Asn Asn Gly Gln Ser Pro Leu Asp Arg Phe Ile
                1               5                   10 tct gtg gta gca tgg tgc ata tct acc act cgc cct gtg act ttt ggt      159
Ser Val Val Ala Trp Cys Ile Ser Thr Thr Arg Pro Val Thr Phe Gly
        15                  20                  25 gtt gct cct tat aat ccc att ctt ggt gag aca cac cat gtt tca agg      207
Val Ala Pro Tyr Asn Pro Ile Leu Gly Glu Thr His His Val Ser Arg
30                  35                  40                  45 gga aat ctt aat gtg tta ttg gag cag att tca cat cac cct cca gta      255
Gly Asn Leu Asn Val Leu Leu Glu Gln Ile Ser His His Pro Pro Val
        50                  55                  60
```

|  |  |  |  |  |  |  |  |  |  |  |  |  |  |  |  |
|---|---|---|---|---|---|---|---|---|---|---|---|---|---|---|---|
| act | gct | ctc | cat | gca | aca | gat | gag | aag | gaa | aac | att | gaa | atg | tta | tgg | 303 |
| Thr | Ala | Leu | His | Ala | Thr | Asp | Glu | Lys | Glu | Asn | Ile | Glu | Met | Leu | Trp |
|  |  |  | 65 |  |  |  | 70 |  |  |  |  | 75 |  |  |  |

| tgc | cag | cga | cct | gat | cca | aag | ttt | aat | ggc | aca | tca | gtt | gaa | gct | aaa | 351 |
| Cys | Gln | Arg | Pro | Asp | Pro | Lys | Phe | Asn | Gly | Thr | Ser | Val | Glu | Ala | Lys |
|  |  | 80 |  |  |  | 85 |  |  |  |  | 90 |  |  |  |  |

| gtg | cat | gga | ata | cgc | cag | ttg | aag | ctc | cta | aat | cat | ggt | gaa | aca | tat | 399 |
| Val | His | Gly | Ile | Arg | Gln | Leu | Lys | Leu | Leu | Asn | His | Gly | Glu | Thr | Tyr |
| 95 |  |  |  |  | 100 |  |  |  |  | 105 |  |  |  |  |  |

| gaa | atg | aat | tgt | cct | cgc | ctt | tta | ctt | aga | att | ctt | cca | gtt | cct | ggt | 447 |
| Glu | Met | Asn | Cys | Pro | Arg | Leu | Leu | Leu | Arg | Ile | Leu | Pro | Val | Pro | Gly |
| 110 |  |  |  | 115 |  |  |  |  | 120 |  |  |  |  | 125 |  |

| gct | gat | tgg | gct | ggt | aca | gtt | aat | ata | cgg | tgc | cta | gag | aca | ggt | cta | 495 |
| Ala | Asp | Trp | Ala | Gly | Thr | Val | Asn | Ile | Arg | Cys | Leu | Glu | Thr | Gly | Leu |
|  |  |  | 130 |  |  |  |  | 135 |  |  |  |  | 140 |  |  |

| gta | gct | gaa | tta | tcc | tac | aga | tca | agt | tct | ttt | cta | gga | att | ggg | ggg | 543 |
| Val | Ala | Glu | Leu | Ser | Tyr | Arg | Ser | Ser | Ser | Phe | Leu | Gly | Ile | Gly | Gly |
|  | 145 |  |  |  |  | 150 |  |  |  |  | 155 |  |  |  |  |

| aat | cat | aga | gtg | atc | aaa | ggg | aag | atc | ctt | gac | tct | tca | tca | ttg | aaa | 591 |
| Asn | His | Arg | Val | Ile | Lys | Gly | Lys | Ile | Leu | Asp | Ser | Ser | Ser | Leu | Lys |
| 160 |  |  |  |  | 165 |  |  |  |  | 170 |  |  |  |  |  |

| gtt | cta | tat | gaa | gtt | gat | ggt | cat | tgg | gat | agg | acc | gta | aaa | gtg | aag | 639 |
| Val | Leu | Tyr | Glu | Val | Asp | Gly | His | Trp | Asp | Arg | Thr | Val | Lys | Val | Lys |
| 175 |  |  |  |  | 180 |  |  |  |  | 185 |  |  |  |  |  |

| gac | aca | aat | aat | ggg | aaa | gta | aga | gtg | ata | tat | gat | gca | aag | gaa | gtt | 687 |
| Asp | Thr | Asn | Asn | Gly | Lys | Val | Arg | Val | Ile | Tyr | Asp | Ala | Lys | Glu | Val |
| 190 |  |  |  | 195 |  |  |  |  | 200 |  |  |  |  | 205 |  |

| atg | tca | ggt | ctc | gaa | act | cct | ata | ctc | aag | gac | ata | gag | ggt | gtg | tgg | 735 |
| Met | Ser | Gly | Leu | Glu | Thr | Pro | Ile | Leu | Lys | Asp | Ile | Glu | Gly | Val | Trp |
|  |  |  | 210 |  |  |  |  | 215 |  |  |  |  | 220 |  |  |

| caa | aca | gaa | tca | gct | cat | gtt | tgg | ggt | gaa | tta | aac | caa | gcc | att | gtg | 783 |
| Gln | Thr | Glu | Ser | Ala | His | Val | Trp | Gly | Glu | Leu | Asn | Gln | Ala | Ile | Val |
|  |  | 225 |  |  |  |  | 230 |  |  |  |  | 235 |  |  |  |

| agc | aaa | gac | tgg | gag | aaa | gca | aga | gaa | gca | aag | cta | aaa | gtt | gag | gaa | 831 |
| Ser | Lys | Asp | Trp | Glu | Lys | Ala | Arg | Glu | Ala | Lys | Leu | Lys | Val | Glu | Glu |
|  | 240 |  |  |  |  | 245 |  |  |  |  | 250 |  |  |  |  |

| aga | caa | agg | gag | ctt | gtg | aga | gaa | aga | gaa | tca | aaa | gga | gaa | aca | tgg | 879 |
| Arg | Gln | Arg | Glu | Leu | Val | Arg | Glu | Arg | Glu | Ser | Lys | Gly | Glu | Thr | Trp |
| 255 |  |  |  |  | 260 |  |  |  |  | 265 |  |  |  |  |  |

| att | tct | aag | cat | ttt | gta | gtt | tct | aac | aac | aaa | gaa | ggg | tgg | caa | tgt | 927 |
| Ile | Ser | Lys | His | Phe | Val | Val | Ser | Asn | Asn | Lys | Glu | Gly | Trp | Gln | Cys |
| 270 |  |  |  | 275 |  |  |  |  | 280 |  |  |  |  | 285 |  |

| tca | cct | att | cat | aag | agt | gta | cct | gcg | gcc | ccc | atc | aca | gcc | cta | taa | 975 |
| Ser | Pro | Ile | His | Lys | Ser | Val | Pro | Ala | Ala | Pro | Ile | Thr | Ala | Leu |
|  |  |  | 290 |  |  |  |  | 295 |  |  |  |  | 300 |  |  |

| ttgttgtcac tgtcaagtag tgtaaagcat taaagtacat tttagaagag aatgttcata | 1035 |
| aaaaaattta atggttgaaa ttttgacaac aatgaagtat ataacaaaat ttaaaattag | 1095 |
| ttacaattt aaaaaaaaaa aaaaaaaaag gcggccgcc g | 1136 |

<210> SEQ ID NO 3
<211> LENGTH: 1355
<212> TYPE: DNA
<213> ORGANISM: Glycine max
<220> FEATURE:
<221> NAME/KEY: CDS
<222> LOCATION: (32)...(1099)

<400> SEQUENCE: 3
ggaattcggc tcgaggacaa tgcttcagaa a atg gct gag ctt atg gag tac    52

-continued

```
                            Met Ala Glu Leu Met Glu Tyr
                             1               5 tct tac ctg tta gat atg gcg gac aag act gag gat cca tac atg aga         100
Ser Tyr Leu Leu Asp Met Ala Asp Lys Thr Glu Asp Pro Tyr Met Arg
         10              15                  20 cta gta tat gct tca tca ttc ttt ata tct gtc tac tat gcc tat caa         148
Leu Val Tyr Ala Ser Ser Phe Phe Ile Ser Val Tyr Tyr Ala Tyr Gln
     25              30                  35 cga acg tgg aag cca ttc aat cca att ctt ggt gag act tat gaa atg         196
Arg Thr Trp Lys Pro Phe Asn Pro Ile Leu Gly Glu Thr Tyr Glu Met
 40              45                  50                  55 gtt aac cat ggt ggc att aca ttt ata tca gag cag gtc agt cat cac         244
Val Asn His Gly Gly Ile Thr Phe Ile Ser Glu Gln Val Ser His His
                 60                  65                  70 cct cca atg agt gct ggg cat gct gaa act gaa cat ttc act tat gat         292
Pro Pro Met Ser Ala Gly His Ala Glu Thr Glu His Phe Thr Tyr Asp
             75                  80                  85 gtt aca tca aaa ttg aaa acc aaa ttt ctc ggc aac tca gtt gat gta         340
Val Thr Ser Lys Leu Lys Thr Lys Phe Leu Gly Asn Ser Val Asp Val
         90                  95                 100 tat cct gtt gga aga acg cgt gtt acc ctc aaa aga gat ggt gtg gtc         388
Tyr Pro Val Gly Arg Thr Arg Val Thr Leu Lys Arg Asp Gly Val Val
    105                 110                 115 ctt gat ttg gtg cct cct cct aca aaa gtt agc aac ttg att ttt gga         436
Leu Asp Leu Val Pro Pro Pro Thr Lys Val Ser Asn Leu Ile Phe Gly
120                 125                 130                 135 cga act tgg att gat tca cca gga gag atg atc ctg aca aat ctg act         484
Arg Thr Trp Ile Asp Ser Pro Gly Glu Met Ile Leu Thr Asn Leu Thr
                140                 145                 150 aca ggg gac aaa gtg gtg ctg tat ttt caa cca tgt ggc tgg ttt gga         532
Thr Gly Asp Lys Val Val Leu Tyr Phe Gln Pro Cys Gly Trp Phe Gly
            155                 160                 165 gct ggt aga tat gaa gtg gat ggg tac gtg tat aat tct gct gac gag         580
Ala Gly Arg Tyr Glu Val Asp Gly Tyr Val Tyr Asn Ser Ala Asp Glu
        170                 175                 180 cct aag ata ctg atg act gga aaa tgg aat gag gct atg aat tat caa         628
Pro Lys Ile Leu Met Thr Gly Lys Trp Asn Glu Ala Met Asn Tyr Gln
    185                 190                 195 gtt tgt gac tca gag gga gaa cca ctt cca ggc act gag ttg aaa gag         676
Val Cys Asp Ser Glu Gly Glu Pro Leu Pro Gly Thr Glu Leu Lys Glu
200                 205                 210                 215 att tgg aga gtt gct gat acc ccg aag aag gac aag ttc cag tac acg         724
Ile Trp Arg Val Ala Asp Thr Pro Lys Lys Asp Lys Phe Gln Tyr Thr
                220                 225                 230 cat ttt gca cac aag att aac agc ttt gac act gct ccc aag aag ttg         772
His Phe Ala His Lys Ile Asn Ser Phe Asp Thr Ala Pro Lys Lys Leu
            235                 240                 245 ttg gca tct gac tct cgt cta cgt cct gat aga atg gcc ctt gag aag         820
Leu Ala Ser Asp Ser Arg Leu Arg Pro Asp Arg Met Ala Leu Glu Lys
        250                 255                 260 ggt gac cta tcc aca tct ggt tat gag aag agc agt ttg gag gag agg         868
Gly Asp Leu Ser Thr Ser Gly Tyr Glu Lys Ser Ser Leu Glu Glu Arg
    265                 270                 275 caa aga gct gag aag aga aac cga gag gcc aag ggc cat aag ttc act         916
Gln Arg Ala Glu Lys Arg Asn Arg Glu Ala Lys Gly His Lys Phe Thr
280                 285                 290                 295 cct aga tgg ttt gat tta aca gat gaa gta act cct acc cct tgg ggt         964
Pro Arg Trp Phe Asp Leu Thr Asp Glu Val Thr Pro Thr Pro Trp Gly
                300                 305                 310
```

-continued

| | |
|---|---|
| gac ttg gaa gtt tac caa tac aac ggt aaa tat acc caa cat tgt gct<br>Asp Leu Glu Val Tyr Gln Tyr Asn Gly Lys Tyr Thr Gln His Cys Ala<br>                315                      320                   325 | 1012 |
| gcc gtt gat agt tct gag tgc att gaa gtg cct gac atc aga cca gaa<br>Ala Val Asp Ser Ser Glu Cys Ile Glu Val Pro Asp Ile Arg Pro Glu<br>      330                      335                      340 | 1060 |
| ttc aac cct tgg caa tat gat aat ttg gat gct gaa tag tgagcatcct<br>Phe Asn Pro Trp Gln Tyr Asp Asn Leu Asp Ala Glu<br>345                      350                    355 | 1109 |
| tgtggaattc tttctatttt tttgaaatat cattttgtta ttaagtttgt aatgtaatct | 1169 |
| tgattggaat gcttgaaatt tggttttgtt tttgggttgt tttatcactg tagtatttga | 1229 |
| ttaattaata gtagctatgt tagttcatca gttcactttg catggataaa tgctagtaga | 1289 |
| gaaattaaag ttaaaaaaaa aaaaaaaaaa aaaaaaaaaa aaaaaaaaaa aaaagggcgg | 1349 |
| ccgccg | 1355 |

<210> SEQ ID NO 4
<211> LENGTH: 1422
<212> TYPE: DNA
<213> ORGANISM: Zea mays
<220> FEATURE:
<221> NAME/KEY: CDS
<222> LOCATION: (1)...(1245)

<400> SEQUENCE: 4

| | |
|---|---|
| atg gct acc aaa gaa gaa gct agc gct gtc ccc gcc gcc agt aaa act<br>Met Ala Thr Lys Glu Glu Ala Ser Ala Val Pro Ala Ala Ser Lys Thr<br>1                  5                    10                 15 | 48 |
| tca tgg agt agc ttc ctg aag tcc atc gca tcc ttc aac ggc gac ctc<br>Ser Trp Ser Ser Phe Leu Lys Ser Ile Ala Ser Phe Asn Gly Asp Leu<br>              20                    25                    30 | 96 |
| tcc tct ctc acc gca ccg ccg ttc atc ctc tca aca acc tct tta acc<br>Ser Ser Leu Thr Ala Pro Pro Phe Ile Leu Ser Thr Thr Ser Leu Thr<br>         35                      40                      45 | 144 |
| gag tat tct gcg tac tgg tgc gaa cat cct gca ctc ttc gtt gcc ccc<br>Glu Tyr Ser Ala Tyr Trp Cys Glu His Pro Ala Leu Phe Val Ala Pro<br>50                    55                    60 | 192 |
| gca cgt gag ccc gat cct gcg aag aga gcg ctc ttg gtg ctg aaa tgg<br>Ala Arg Glu Pro Asp Pro Ala Lys Arg Ala Leu Leu Val Leu Lys Trp<br>65                    70                    75                    80 | 240 |
| ttc ctg agc aca ttg cac caa cag tac tgc tct cga agc gaa aag cta<br>Phe Leu Ser Thr Leu His Gln Gln Tyr Cys Ser Arg Ser Glu Lys Leu<br>              85                    90                    95 | 288 |
| gga agc gag aaa aag ccg ctc aac ccg ttc ctg ggc gag ctt ttc ctg<br>Gly Ser Glu Lys Lys Pro Leu Asn Pro Phe Leu Gly Glu Leu Phe Leu<br>         100                      105                    110 | 336 |
| ggc aag tgg ata gag gat gag gat gtg ggc gag aca agg ttg atc agc<br>Gly Lys Trp Ile Glu Asp Glu Asp Val Gly Glu Thr Arg Leu Ile Ser<br>              115                    120                    125 | 384 |
| gag caa gtc agc cat cat cct cct gcg aca gcg tat tca ata gtc aat<br>Glu Gln Val Ser His His Pro Pro Ala Thr Ala Tyr Ser Ile Val Asn<br>130                  135                    140 | 432 |
| gag aaa cat gga gtt gag ctc caa gga tac aac gcc caa aaa gcc tcc<br>Glu Lys His Gly Val Glu Leu Gln Gly Tyr Asn Ala Gln Lys Ala Ser<br>145                  150                  155                160 | 480 |
| ttc tcc agc acc atc caa gtg aaa caa cta ggc cac gcc tat ctc tcc<br>Phe Ser Ser Thr Ile Gln Val Lys Gln Leu Gly His Ala Tyr Leu Ser<br>                165                    170                    175 | 528 |
| tta acg ccg ccc gga aaa gat gca aac aac gaa gac gac cgt gag cac<br>Leu Thr Pro Pro Gly Lys Asp Ala Asn Asn Glu Asp Asp Arg Glu His | 576 |

```
                         180                   185                   190
tac ctc atc acc ctc ccc aac ctc cac atc gaa tcc ctg atc tat ggg      624
Tyr Leu Ile Thr Leu Pro Asn Leu His Ile Glu Ser Leu Ile Tyr Gly
            195                   200                   205 aca cca ttc gtt gaa ttg gaa aag agt tgc aag atc gcc agc tca acc      672
Thr Pro Phe Val Glu Leu Glu Lys Ser Cys Lys Ile Ala Ser Ser Thr
    210                   215                   220 ggg tac atc tct aag ata gac ttt tcg ggc aaa ggc tgg ctg agc gga      720
Gly Tyr Ile Ser Lys Ile Asp Phe Ser Gly Lys Gly Trp Leu Ser Gly
225                   230                   235                   240 aag aaa aat acc ttc tcc gca gtg tta tac aag gaa agc gac ggc gaa      768
Lys Lys Asn Thr Phe Ser Ala Val Leu Tyr Lys Glu Ser Asp Gly Glu
                245                   250                   255 aaa aat cct tta tac aca gcc gac ggt caa tgg tcg agc agc ttc act      816
Lys Asn Pro Leu Tyr Thr Ala Asp Gly Gln Trp Ser Ser Ser Phe Thr
            260                   265                   270 atc cgc gat gca cgc gct aag aag gat att gag acc ttc act atc agc      864
Ile Arg Asp Ala Arg Ala Lys Lys Asp Ile Glu Thr Phe Thr Ile Ser
    275                   280                   285 aat ctg aaa aca acc ccc tta aca gtc gcc cct ctt gat gaa caa gat      912
Asn Leu Lys Thr Thr Pro Leu Thr Val Ala Pro Leu Asp Glu Gln Asp
290                   295                   300 gaa tgg gaa act cgc cgt gca tgg cgc gac gta gca gcc gcc atc gaa      960
Glu Trp Glu Thr Arg Arg Ala Trp Arg Asp Val Ala Ala Ala Ile Glu
305                   310                   315                   320 cgc ggc gac atg gaa gcc aca tca aac gcc aaa acc aag atc gaa gtc     1008
Arg Gly Asp Met Glu Ala Thr Ser Asn Ala Lys Thr Lys Ile Glu Val
                325                   330                   335 gcg caa cga gaa ctc cgc aaa aag gag aaa gag caa ggc gag gag tgg     1056
Ala Gln Arg Glu Leu Arg Lys Lys Glu Lys Glu Gln Gly Glu Glu Trp
            340                   345                   350 gaa cga cga ttc ttc aag cga gtc aac gaa aag gat gaa cct acc ttt     1104
Glu Arg Arg Phe Phe Lys Arg Val Asn Glu Lys Asp Glu Pro Thr Phe
    355                   360                   365 atg aga ttg gcg gcg atg ctg gat ttg acg caa ggc atc gaa agt gac     1152
Met Arg Leu Ala Ala Met Leu Asp Leu Thr Gln Gly Ile Glu Ser Asp
370                   375                   380 cgc acc ggg gga gtt tgg agg ttt gat cct tca cgt gct gtg gat gcg     1200
Arg Thr Gly Gly Val Trp Arg Phe Asp Pro Ser Arg Ala Val Asp Ala
385                   390                   395                   400 aat ccg ccg tat cac aag gtt ggc ggc gaa ggg ttg gga ttg taa         1245
Asn Pro Pro Tyr His Lys Val Gly Gly Glu Gly Leu Gly Leu
                405                   410 tttatttatg aggcatcttt tatatttcat aaaaacaggg tctaggccgt ttattcatta   1305
aatgtgtatt aagtagcgct ttttctcgac cgttgagatt catggatgca agtgtaccta   1365
atagctcaat gcgagactct ttccaagcaa aaaaaaaaaa aaaaaagggg cggccgc      1422

<210> SEQ ID NO 5
<211> LENGTH: 2126
<212> TYPE: DNA
<213> ORGANISM: Saccharomyces cerevisiae
<220> FEATURE:
<221> NAME/KEY: CDS
<222> LOCATION: (453)...(1757)

<400> SEQUENCE: 5
aacctctccg cccgtatatt ttttttaata tgttaaatag tgatagaact gataagcctc     60
attttctttt attgggctcc aagacgcgaa ctgttcgtag ggtaaccgtt tgacacctaa    120
```

```
acgaccttc agcctcacct gcagtatttc ttcaacaacg cctgtcgcta tgttaaataa        180
tagcaatcgt ttgtgatcac cattgtcgaa tttgacgcgc ttaaacaaaa accattgttt        240
tggcctcgtt ccctgcattc aacaaaagag caaggtatgc cgtcaaacag tcgttaaaag        300
agaaggttta taactatctc tgttttgtac tttgctgtcc cggatccagt tgggtcttct        360
tttcaacctg tctgagtccg atctttcttt ccctacttga agctccatat atctaagtca        420
tctaagtgta tcctgctaga ttacaaacga aa atg tct caa cac gca agc tca        473
                                   Met Ser Gln His Ala Ser Ser
                                    1               5 tct tct tgg act tct ttt ttg aaa tcg ata agt tcg ttc aac gga gat        521
Ser Ser Trp Thr Ser Phe Leu Lys Ser Ile Ser Ser Phe Asn Gly Asp
        10                  15                  20 cta tcg tct ttg tct gca cca ccg ttt att ctt tct ccc act tcc tta        569
Leu Ser Ser Leu Ser Ala Pro Pro Phe Ile Leu Ser Pro Thr Ser Leu
     25                  30                  35 aca gag ttt tct cag tat tgg gct gaa cat cca gct tta ttt ctg gag        617
Thr Glu Phe Ser Gln Tyr Trp Ala Glu His Pro Ala Leu Phe Leu Glu
40                  45                  50                  55 cct tcg ttg att gat ggt gaa aac tac aaa gat cac tgt ccc ttt gac        665
Pro Ser Leu Ile Asp Gly Glu Asn Tyr Lys Asp His Cys Pro Phe Asp
                 60                  65                  70 cca aat gtg gaa tca aag gaa gtg gcg cag atg ttg gcg gtt gtt agg        713
Pro Asn Val Glu Ser Lys Glu Val Ala Gln Met Leu Ala Val Val Arg
             75                  80                  85 tgg ttt att tct act ttg aga tct caa tac tgc tct aga agc gaa tcg        761
Trp Phe Ile Ser Thr Leu Arg Ser Gln Tyr Cys Ser Arg Ser Glu Ser
         90                  95                 100 atg ggt tct gaa aag aag cct ttg aac cca ttc ttg ggt gag gta ttt        809
Met Gly Ser Glu Lys Lys Pro Leu Asn Pro Phe Leu Gly Glu Val Phe
    105                 110                 115 gtt gga aag tgg aaa aat gat gag cat cca gag ttt ggt gaa acg gtt        857
Val Gly Lys Trp Lys Asn Asp Glu His Pro Glu Phe Gly Glu Thr Val
120                 125                 130                 135 ctt tta agt gag caa gtt tca cat cat cca cct atg aca gca ttt tcg        905
Leu Leu Ser Glu Gln Val Ser His His Pro Pro Met Thr Ala Phe Ser
                140                 145                 150 att ttt aat gaa aaa aat gat gtt tct gtt caa gga tac aat caa att        953
Ile Phe Asn Glu Lys Asn Asp Val Ser Val Gln Gly Tyr Asn Gln Ile
            155                 160                 165 aaa act ggt ttt acc aaa aca ttg acg cta acg gtc aaa cca tac ggg       1001
Lys Thr Gly Phe Thr Lys Thr Leu Thr Leu Thr Val Lys Pro Tyr Gly
        170                 175                 180 cat gtc att ttg aag att aaa gat gag acc tac ctg att aca acc ccg       1049
His Val Ile Leu Lys Ile Lys Asp Glu Thr Tyr Leu Ile Thr Thr Pro
    185                 190                 195 cct ttg cat atc gaa ggt att tta gtc gct tct cca ttt gtt gaa tta       1097
Pro Leu His Ile Glu Gly Ile Leu Val Ala Ser Pro Phe Val Glu Leu
200                 205                 210                 215 gga ggc agg tca ttc ata cag tca tca aat ggt atg tta tgt gtt ata       1145
Gly Gly Arg Ser Phe Ile Gln Ser Ser Asn Gly Met Leu Cys Val Ile
                220                 225                 230 gaa ttt tca gga agg ggg tat ttc aca ggg aag aag aac tcc ttt aag       1193
Glu Phe Ser Gly Arg Gly Tyr Phe Thr Gly Lys Lys Asn Ser Phe Lys
            235                 240                 245 gca aga att tac aga agc cca caa gag cat agt cat aaa gaa aat gcg       1241
Ala Arg Ile Tyr Arg Ser Pro Gln Glu His Ser His Lys Glu Asn Ala
        250                 255                 260 cta tac cta atc tct ggc caa tgg tca ggt gtt tca aca att ata aaa       1289
```

```
                    Leu Tyr Leu Ile Ser Gly Gln Trp Ser Gly Val Ser Thr Ile Ile Lys
                        265                 270                 275 aaa gac tcg caa gtt tca cat cag ttt tac gat tca tcg gaa act cct             1337
Lys Asp Ser Gln Val Ser His Gln Phe Tyr Asp Ser Ser Glu Thr Pro
280                 285                 290                 295 act gaa cat tta tta gtt aag cca atc gaa gaa caa cat cct ctg gaa             1385
Thr Glu His Leu Leu Val Lys Pro Ile Glu Glu Gln His Pro Leu Glu
                300                 305                 310 agt agg agg gca tgg aag gat gtg gca gaa gca atc aga caa gga aat             1433
Ser Arg Arg Ala Trp Lys Asp Val Ala Glu Ala Ile Arg Gln Gly Asn
            315                 320                 325 att agt atg ata aaa aag act aag gaa gaa cta gaa aat aag caa aga             1481
Ile Ser Met Ile Lys Lys Thr Lys Glu Glu Leu Glu Asn Lys Gln Arg
        330                 335                 340 gcc ttg aga gaa caa gaa cgc gta aaa ggt gtg gaa tgg caa aga aga             1529
Ala Leu Arg Glu Gln Glu Arg Val Lys Gly Val Glu Trp Gln Arg Arg
    345                 350                 355 tgg ttc aaa caa gtg gac tac atg aat gaa aat aca tca aat gat gta             1577
Trp Phe Lys Gln Val Asp Tyr Met Asn Glu Asn Thr Ser Asn Asp Val
360                 365                 370                 375 gag aaa gca agt gaa gat gat gcc ttt agg aaa ttg gcg tcc aaa ctg             1625
Glu Lys Ala Ser Glu Asp Asp Ala Phe Arg Lys Leu Ala Ser Lys Leu
                380                 385                 390 cag ctt tct gtg aaa aat gtg cca agt ggg aca ttg att ggc ggc aaa             1673
Gln Leu Ser Val Lys Asn Val Pro Ser Gly Thr Leu Ile Gly Gly Lys
            395                 400                 405 gat gat aag aaa gat gtt tca acc gca ttg cat tgg agg ttt gat aaa             1721
Asp Asp Lys Lys Asp Val Ser Thr Ala Leu His Trp Arg Phe Asp Lys
        410                 415                 420 aat ttg tgg atg agg gag aac gaa att act ata taa tataaatgtt                  1767
Asn Leu Trp Met Arg Glu Asn Glu Ile Thr Ile
    425                 430 tttaaaagaa taaatatcaa aaattaatac taattgatgt ttgcattgct ttttttaagg           1827
gaaaatgcaa gcgttttttat ttttaacttt tggttttgaa gctcgtaatt caacaaaaaa          1887
gaattaaata atcttcaagt ccgataacaa gatgtagaaa aaacatccca atgaagttac           1947
aagtcaaacc attcactgag aatttttgta actcaccacc gatttttggg ataaaatgta           2007
ttcctgcaac ttttttttttt gaagagataa aaagaattga atagaatatg cagtaaaaaa          2067
agaatctcga aaaaaaaagg acaagaaatc ttaactacca tcaaacaatt gaaaattga            2126

<210> SEQ ID NO 6
<211> LENGTH: 266
<212> TYPE: DNA
<213> ORGANISM: Glycine max

<400> SEQUENCE: 6
ccattcaatc caattcttgg tgagacttat gaaatggtta accatggtgg cattacattt            60
atatcagagc aggtcagtca tcaccctcca atgagtgctg gcatgctga aactgaacat            120 ttcactatg atgttacatc aaaattgaaa accaaatttc tcggcaactc agttgatgta            180
tatcctgttg gaagaacgcg tgttaccctc aaaagagatg gtgtggtcct tgatttggtg          240
cctcctccta caaagttag caactt                                                266

<210> SEQ ID NO 7
<211> LENGTH: 291
<212> TYPE: DNA
<213> ORGANISM: Glycine max
<220> FEATURE:
```

```
<221> NAME/KEY: unsure
<222> LOCATION: (1)...(291)
<223> OTHER INFORMATION: Unsure at all n locations

<400> SEQUENCE: 7
tcacaacttc agtgctatgg tgaatcagtg tattgcacag gttcggactt gctaagcatg      60
tgcaacaatg gtcagagtcc acttgatagg ttcatatctg tggtagcatg gtgcatatct     120
accactcgcc ctgtgacttt tggtgttgct ccttataatc ccantcttgg tgagacacac     180
cncgtttcaa ggggaaatct taatgtgtta ttggagcaga tttcacatca ccctccagta     240
actgctctcc atgcaacaga tgagangaa acattgaaa tgttatggtg c                291

<210> SEQ ID NO 8
<211> LENGTH: 282
<212> TYPE: DNA
<213> ORGANISM: Glycine max
<220> FEATURE:
<221> NAME/KEY: unsure
<222> LOCATION: (1) ... (282)
<223> OTHER INFORMATION: Unsure at all n locations

<400> SEQUENCE: 8
gtgcccagng acaggtctgg tagctgaaat atcatacatg atcaagccat tgcttttta      60 ggatttnggg gaagtcgtaa attgatcaaa gggnaaatcc ttgactcatn attactcaaa    120
ggtctctgcg aagttgatng tcattgggat aagatagtta gagtgaagga tacnaatagt    180
gnagaagtga gagtgatata tgatgccaaa gaagccnttt caggtctcaa aactcctatt    240
atcaaggatg tggagagtgt gtggccaacc gaatcagccc tt                       282

<210> SEQ ID NO 9
<211> LENGTH: 255
<212> TYPE: DNA
<213> ORGANISM: Glycine max

<400> SEQUENCE: 9
gtaactccta cccctggggg tgacttggaa gtttaccaat acaacggtaa atatacccaa      60
cattgtgctg ccgttgatag ttctgagtgc attgaagtgc ctgacatcag accagaattc    120
aaccccttgg caatatgataa tttggatgct aatagtgag catccttgtg gaattctttc    180
tatttttttt aaatatcatt ttgttattaa gtttgtaatg taatcttgat tggaagcttg    240
aaatttggtt ttgtt                                                     255

<210> SEQ ID NO 10
<211> LENGTH: 250
<212> TYPE: DNA
<213> ORGANISM: Glycine max

<400> SEQUENCE: 10
taactcctac cccttggggt gacttggaag tttaccaata caacggtaaa tatacccaac      60
attgtgctgc cgttgatagt tctgagtgca ttgaagtgcc tgacatcaga ccagaattca    120
acccttggca atatgataat ttggatgctg aatagtgagc atccttgtgg aattctttct    180
atttttttta aatatcattt tgttattaag tttgtaatgt aatcttgatt ggaatgcttg    240
aaatttggtt                                                           250

<210> SEQ ID NO 11
<211> LENGTH: 283
<212> TYPE: DNA
<213> ORGANISM: Glycine max
```

```
<220> FEATURE:
<221> NAME/KEY: unsure
<222> LOCATION: (1) ... (283)
<223> OTHER INFORMATION: Unsure at all n locations

<400> SEQUENCE: 11
cgcctgtgnt taatttccca aaatctcaac ttcaatgcta nggtgaatca gtgtactgca      60
catcttccaa cttgctaagc caatgcaaac agtgggcaga gtccactgga caggttcaca     120
tcagtagtag catggagcat atctaccaca cgccccacat cttttggtgt tgctccttat     180
aattccactc ttggagagac ccaccatgtt tccaagggca atctcaacgt cctagttgag     240
caggtttcac tcaatcctcc agtatctgcc ctccatgcaa cag                       283

<210> SEQ ID NO 12
<211> LENGTH: 255
<212> TYPE: DNA
<213> ORGANISM: Glycine max

<400> SEQUENCE: 12
ggagagtgtg tggccaaccg aatcagccct tgtttggagt gagttgagcc aagccattat      60
gaacaaagat tgggaaagag caagagaagc aaagcaagac gtggaagaaa gacagaggaa     120
tatgttgaga gacagagcca tgaaggagaa acttggtttt cctaagaatt ttagggtgtc     180
ttacagtaaa gacacatggg aatgggactg ttcaccaact cataaatggg tccctgaggc     240
ccccatcata gctca                                                      255

<210> SEQ ID NO 13
<211> LENGTH: 259
<212> TYPE: DNA
<213> ORGANISM: Glycine max
<220> FEATURE:
<221> NAME/KEY: unsure
<222> LOCATION: (1) ... (259)
<223> OTHER INFORMATION: Unsure at all n locations

<400> SEQUENCE: 13
agtcaaccct ccagtatctg ccctccatgc aacagatgag anggaaaaca ttgagatgat      60
atggtcccag caacctgttc caaagtttcg gggtacatct atgaagctca agtgcatggt     120
aaacgtcata tgtttctcca tgatttagga gcttcagctg acgttaccaa tgcacttgag     180
ctgangctcc taaatcatgg agaaacatat gaaatgaatt gtcctcacct ttcaattaga     240
attcttccgg ttcctggga                                                  259

<210> SEQ ID NO 14
<211> LENGTH: 355
<212> TYPE: DNA
<213> ORGANISM: Glycine max
<220> FEATURE:
<221> NAME/KEY: unsure
<222> LOCATION: (1) ... (355)
<223> OTHER INFORMATION: Unsure at all n locations

<400> SEQUENCE: 14
gcagcttttg ctgtgtctag ctatgcgtca actgaangtc gacaatgtaa acctttaat       60 cctttactcg gggagaccta cgaagctgac tatccagata aaggacttaa gttttttct      120 gaaaaggtta gtcatcatcc aatgattgtt gcttgtcact gtgagggaag gggatggaag     180
ttttgggcag attctaattt gaaaggaaaa ttctgggggc gttctatcca gttagatcct     240
gtgggtgtcc tcactctaca gtttgaggat ggtgaaacat ttcagtggag caaggtcacc     300
```

```
acttcgattt acaatatcat actangtaaa atttattgtg accactacgg tacca        355
```

<210> SEQ ID NO 15
<211> LENGTH: 279
<212> TYPE: DNA
<213> ORGANISM: Glycine max
<220> FEATURE:
<221> NAME/KEY: unsure
<222> LOCATION: (1)...(279)
<223> OTHER INFORMATION: Unsure at all n locations

<400> SEQUENCE: 15

```
cagattcgga ggaggaagct cagagaggaa gatggaaaca ggaggaaaga gatggttact    60
ggaagatgat gcagaagtat attggctcgg atgtaacatc aatggtgaca ctaccagtta   120
ttatatttga accaatgact atgattcaga aaattgctga gttgatggag tactcctact   180
tgttagatca agcagatgaa tcagaggatc catacatgca gttagtttat gcaatggatg   240
tacttnatgt atcatcacag catccatggg ccatatcgg                          279
```

<210> SEQ ID NO 16
<211> LENGTH: 191
<212> TYPE: DNA
<213> ORGANISM: Glycine max

<400> SEQUENCE: 16

```
gttgatagtt ctgagtgcat agaggtgcct gacagcagaa cagaattcaa cccttggcaa    60
tatgataatt tggatgctga ataataagca tccttgtaga attctttcta ttcttttgaac  120
tatcattttg ttattaagtt tgcaatgtat ctgattggaa tgcttgaaat ttggttttgt   180
ttttgggtaa a                                                        191
```

<210> SEQ ID NO 17
<211> LENGTH: 267
<212> TYPE: DNA
<213> ORGANISM: Glycine max
<220> FEATURE:
<221> NAME/KEY: unsure
<222> LOCATION: (1)...(267)
<223> OTHER INFORMATION: Unsure at all n locations

<400> SEQUENCE: 17

```
tcaactcctt ggggtgattt ggaaatctat caatataatg gtaaatacag tgaacatcga    60
gctgctgcag ataactcagg aagcattgat gatgttgatg ctaaatcaat tgaattcaat   120
ccatggcagt atggtaattt ggccacggaa tgaactagtt tcaatttctt tggttttgga   180
tgntncagtt agttcatgta actnttnncn antganacna gaanacaact ncctncnnca   240
ncnnanngtt agttgggcng tgtacgc                                       267
```

<210> SEQ ID NO 18
<211> LENGTH: 252
<212> TYPE: DNA
<213> ORGANISM: Glycine max

<400> SEQUENCE: 18

```
gtcttataga gctcccaatc tcctacatcg cttgttaagt ttactcaaga acgtgcggcc    60
aggatcagat ctcacacact tccaactgcc agctgtgttt aacttcccaa aatctcaact   120
tcaatgctat ggtgaatcag tgtactgcac atcttcaaac ttgctgagca aatgcaacaa   180
tgggcagagt ccactggaca ggttcacatc agtagtagca tggagcatat ctaccacacg   240
ccccacatct tt                                                       252
```

<210> SEQ ID NO 19
<211> LENGTH: 241
<212> TYPE: DNA
<213> ORGANISM: Glycine max

<400> SEQUENCE: 19

| | | |
|---|---|---|
| gtcagtcatc acccctccaat gagtgctggg catgctgaaa ctgaacattt cacttatgat | 60 |
| gttacatcaa aattgaaaac caaatttctc ggcaactcag ttgatgtata tcctgttgga | 120 |
| agaacgcgtg ttaccctcaa aagagatggt gtggtccttg atttggtgcc tcctcctaca | 180 |
| aaagttagca acttgatttt tggacgaact tggattgatt caccaggaga gatgatcctg | 240 |
| a | 241 |

<210> SEQ ID NO 20
<211> LENGTH: 262
<212> TYPE: DNA
<213> ORGANISM: Glycine max

<400> SEQUENCE: 20

| | | |
|---|---|---|
| tctcgagcct attcggctcg aggccaaaga agccatttca ggtcactaaa ctcctattat | 60 |
| catatgatgt ggagagtgtg tattcaaccg aatcagccct tgtttggagt gagttgagcc | 120 |
| aagccattat gaacaaagat tgggaaagag caagagaagc aaagcaagac gtggaagaaa | 180 |
| gacagaggaa tatgttgaga cacagagcca tgacaggaga aactggttgt ctaagaattt | 240 |
| agggtgtctt acagtaaaga ca | 262 |

<210> SEQ ID NO 21
<211> LENGTH: 463
<212> TYPE: DNA
<213> ORGANISM: Arabidopsis thaliana
<220> FEATURE:
<221> NAME/KEY: unsure
<222> LOCATION: (1) ... (463)
<223> OTHER INFORMATION: Unsure at all n locations

<400> SEQUENCE: 21

| | | |
|---|---|---|
| ggggaacccc ttccaggaac agagctgaaa gaggtgtggc atttggctga tgtccccaaa | 60 |
| aacgacaact tcagtacac tcactttgct cacaagataa acagcttcga cacagcgcct | 120 |
| gctaagctct tggcttcaga ctcacgtatc cgtcctgata gatattccct tgagcagggt | 180 |
| gacctttcta aagctggttc cgagaaacac agccttgagg agagacaaag ggccgaaaag | 240 |
| aggaccagag agacaaaggg acaaaagttc actccaagat ggttcgatct aacggatgag | 300 |
| atcacaccta ctccatgggg agatattgaa gtataccant acaacgggaa gtacaatgaa | 360 |
| caccgagaca cggcagagag ctcaagtagt gcctccaacg aaacgggact caaatccatc | 420 |
| gagtttaatc cttggcaata tggtaatatc tcaaccgaat gaa | 463 |

<210> SEQ ID NO 22
<211> LENGTH: 399
<212> TYPE: DNA
<213> ORGANISM: Arabidopsis thaliana

<400> SEQUENCE: 22

| | | |
|---|---|---|
| agtgaacctc tcccaggcac cgaactgaaa gaggtatgga aactcgctga tgtgccaaag | 60 |
| gatgacaaat atcaatacac tcactttgct cacaagatta atagcttcga cactgccccg | 120 |
| aaaaagctgt tgccctctga ttcacggtta cgacctgata gatacgcact tgagatgggc | 180 |

```
gacatgtcca aatcaggcta tgagaagagc agcatggaag agagacagag agctgacaag    240
agaacccgcg aacataaagg ccaagccttt actccaaaat ggttcgatgt aacggaagaa    300
gtcactgcta caccatgggg tgatctggaa gtttaccaat tcactggaaa gtactcagaa    360
catcgtgcag ctgcggataa ctctgaagat aagaccgac                           399
```

<210> SEQ ID NO 23
<211> LENGTH: 343
<212> TYPE: DNA
<213> ORGANISM: Arabidopsis thaliana

<400> SEQUENCE: 23

```
acggacgcgt gggcaactcc aatgttacgg cgagatggtc tacagcttcg tcggtcagga     60
tctgcttggg gaatgcagcc gccgtgatct tcccattgaa cggctcaaat cagtggtgac    120
gtggaacatc tccacactcc gtccggtggt ctttggcatg tctccgtaca actccgttct    180
cggcgagact caccacgtat cgaacggtca catcaacgtc atcgccgaac aagtagtgca    240
tcatcctccg gtttccgctc ttcatgcgac tcacgaacaa gaaaatatcg acgtgacatg    300
gtgtcaatat ttcactccta aatttcgtgg tactcacgtg gac                      343
```

<210> SEQ ID NO 24
<211> LENGTH: 510
<212> TYPE: DNA
<213> ORGANISM: Arabidopsis thaliana
<220> FEATURE:
<221> NAME/KEY: unsure
<222> LOCATION: (1) ... (510)
<223> OTHER INFORMATION: Unsure at all n locations

<400> SEQUENCE: 24

```
gaaagctagc agatgtagaa caaagttttt tgtaactacg agagaataag aatacatttg     60
tttccaaaaa gatttgatct tttctgtctt tggagcgat  acatttaagt agacagatct    120
tggaattgcc atgggttgaa ttggatcgac ttagggtcgg tgttatcttc agagttatcc    180
gcagctgcac gatgttccga gtactttcca ttgaattggt aaacttccag atcaccccat    240
ggtgtagcag tgacttcttc cgttacatcg aaccattttg gagtaaaggc ttggcctttc    300
tcttcgcggg gtcncttttc aagtctctgt cnctcttcca tggtgntctt cccanagcct    360
gatttgnaca tggcggccan cccaagggng atcaatcag gccgnaacgg ggaatcagnn     420
ggnaacagct tttcngggna ntgncgaagc aataaaccnt ggggcaaag ggggggatt      480 ggaaattggc aacccttggn naacagggc                                      510
```

<210> SEQ ID NO 25
<211> LENGTH: 282
<212> TYPE: DNA
<213> ORGANISM: Arabidopsis thaliana
<220> FEATURE:
<221> NAME/KEY: unsure
<222> LOCATION: (1) ... (282)
<223> OTHER INFORMATION: Unsure at all n locations

<400> SEQUENCE: 25

```
gatacatttg gattcgaaaa gagcagccta gaggatagac aaagagctga gaagaaaagc     60
agagaagaga aaggccaaaa ntttccncca aaatggtttn atgaaacana agangtcact    120
cctacaccat ggggtgatct cgaagtttac caattcantg gaaagtactc ggtgcaccgn    180
gccacagctg aaaactntga ggatacaacc gntgtgaagt tgnncccaatt caacccttgg    240 caattccaag atctctntgc ttaatccttt ggtgccattt gt                       282
```

<210> SEQ ID NO 26
<211> LENGTH: 380
<212> TYPE: DNA
<213> ORGANISM: Arabidopsis thaliana
<220> FEATURE:
<221> NAME/KEY: unsure
<222> LOCATION: (1) ... (380)
<223> OTHER INFORMATION: Unsure at all n locations

<400> SEQUENCE: 26

```
cgttggtggc ngcggaagtg gtttcttcgc ctctcttgct tcgtcgatct ccaatttngg    60
ntctgctatg accaaatcag ttaatggttt ggttccctat gagggacttg aagttatcaa   120
tcctgaagga agtacagatg atgctgagga ggaagcaagc agaggaagat ggaagcaaga   180
ggatcgagat ggctattgga agatgatgca gaagtacata ggatctgatg ttacatcaat   240
ggtgacccct cctgtgatta ttttgaacc aatgacaatg cttcagaaaa tggcggagtt   300
gatggaatac tcgcatctgc tagacatggc agacaaaacc gaggacccett attcgcat   360
ggtgtatgca tcatcgtggg                                               380
```

<210> SEQ ID NO 27
<211> LENGTH: 359
<212> TYPE: DNA
<213> ORGANISM: Arabidopsis thaliana
<220> FEATURE:
<221> NAME/KEY: unsure
<222> LOCATION: (1) ... (359)
<223> OTHER INFORMATION: Unsure at all n locations

<400> SEQUENCE: 27

```
ggtaatgaag gagttgaggt cataaatcca gaaggtggca aggaagatnc tgaagaggaa    60
gctcagaaag gaaggtggaa ggacgaggaa cgagatagtt actggaagat gatgcagaaa   120
tataggtt cggatattac gtcaatggtg gctcttcctg ttgtnatatt tnanccatg    180
actatnctcc anaagatggc tgagataatg gagtattctc atttnttgga tcaagcagat   240
gaatgcngag atccatactt gctgttagta tatccttcat catggggtat atctgtttac   300
tatggccttc caacggacct tggaagcctt tnaatccnat tcttggggg gnnanttna    359
```

<210> SEQ ID NO 28
<211> LENGTH: 510
<212> TYPE: DNA
<213> ORGANISM: Arabidopsis thaliana
<220> FEATURE:
<221> NAME/KEY: unsure
<222> LOCATION: (1) ... (510)
<223> OTHER INFORMATION: Unsure at all n locations

<400> SEQUENCE: 28

```
aaaagagaaa agtgttagcc tttggtcaat gatcaaagac antatagga aggntctcac    60
aaaagtctgt cttcctgttt acttcaacga gccactttct tctttacaga aatgttttga   120
ggatttggaa tattcgtacc ttcttgaccg agcatttgaa tatggcaaaa ggggaaatag   180
cctcatgagg atacttaatg tagctgcttt tgctgtatct gggtatgcat caactgaagg   240
aagaatttgc aaacctttta atccattgtt aggtgaaaca tacgnggcag actatccaga   300
caaaggcctt cggttttttt ccaggaaagg tcagtcatca tcctatggtt gtcgnatgcc   360
attgtgatgg caccnggtgg gaattcttgg gggacagcaa tcttngggc aaatttnggg   420
gcgntctntt tagcttnacc cccttgggga ttnnccttna aattnatgat ggggaanccn   480
```

```
cagggggaa ggngcccacc atnncaaacc                                      510
```

<210> SEQ ID NO 29
<211> LENGTH: 493
<212> TYPE: DNA
<213> ORGANISM: Arabidopsis thaliana
<220> FEATURE:
<221> NAME/KEY: unsure
<222> LOCATION: (1) ... (493)
<223> OTHER INFORMATION: Unsure at all n locations

<400> SEQUENCE: 29

```
ccccncccng aaagnttccc ctgtttccgg nttnncccnt ntgnncccccc ttggggggn      60 cctttcccaa tnggnnttgg gngngccccc ttggangggg ccgggctttt aagggcccc     120 ncgnagggaa ggccagcctt tctcccaaat ggtcgatgta ccggaggaag tcactgctac    180 cccatgggt gatctggaag tttcccaatt caatggaaag tactcggaac atcgtgcagc    240
tgcggataac tctgaagata caccgaccc taagtcgatc caattcaacc catggcaatt    300
ccaagatctg tctacttaaa tgtatcgctc caaaagacag aaaagatcaa atcttttgg    360 aaacaaatgt attcttattc tctcgtagtt acaaaaaact tgttctaca tctgctagct    420 ttcccattgc tttctctagt attagtgtac aacttctact gttttgtctt aaattcattc    480
aaatctttct ttg                                                       493
```

<210> SEQ ID NO 30
<211> LENGTH: 358
<212> TYPE: PRT
<213> ORGANISM: Glycine max

<400> SEQUENCE: 30

```
Met Thr Met Leu Gln Lys Met Ala Glu Leu Met Glu Tyr Ser Tyr Leu
1               5                   10                  15

Leu Asp Met Ala Asp Lys Thr Glu Asp Pro Tyr Met Arg Leu Val Tyr
            20                  25                  30

Ala Ser Ser Phe Phe Ile Ser Val Tyr Tyr Ala Tyr Gln Arg Thr Trp
        35                  40                  45

Lys Pro Phe Asn Pro Ile Leu Gly Glu Thr Tyr Glu Met Val Asn His
    50                  55                  60

Gly Gly Ile Thr Phe Ile Ser Glu Gln Val Ser His Pro Pro Met
65                  70                  75                  80

Ser Ala Gly His Ala Glu Thr Glu His Phe Thr Tyr Asp Val Thr Ser
                85                  90                  95

Lys Leu Lys Thr Lys Phe Leu Gly Asn Ser Val Asp Val Tyr Pro Val
            100                 105                 110

Gly Arg Thr Arg Val Thr Leu Lys Arg Asp Gly Val Val Leu Asp Leu
        115                 120                 125

Val Pro Pro Thr Lys Val Ser Asn Leu Ile Phe Gly Arg Thr Trp
    130                 135                 140

Ile Asp Ser Pro Gly Glu Met Ile Leu Thr Asn Leu Thr Thr Gly Asp
145                 150                 155                 160

Lys Val Val Leu Tyr Phe Gln Pro Cys Gly Trp Phe Gly Tyr Glu Val
                165                 170                 175

Asp Gly Tyr Val Tyr Asn Ser Ala Asp Glu Pro Lys Ile Leu Met Thr
            180                 185                 190

Gly Lys Trp Asn Glu Ala Met Asn Tyr Gln Val Cys Asp Ser Glu Gly
        195                 200                 205
```

```
Glu Pro Leu Pro Gly Thr Glu Leu Lys Glu Ile Trp Arg Val Ala Asp
    210                 215                 220

Thr Pro Lys Lys Asp Lys Phe Gln Tyr Thr His Phe Ala His Lys Ile
225                 230                 235                 240

Asn Ser Phe Asp Thr Ala Pro Lys Lys Leu Leu Ala Ser Asp Ser Arg
                245                 250                 255

Leu Arg Pro Asp Arg Met Ala Leu Glu Lys Gly Asp Leu Ser Thr Ser
            260                 265                 270

Gly Tyr Glu Lys Ser Ser Leu Glu Glu Arg Gln Arg Ala Glu Lys Arg
        275                 280                 285

Asn Arg Glu Ala Lys Gly His Lys Phe Thr Pro Arg Trp Phe Asp Leu
    290                 295                 300

Thr Asp Glu Val Thr Pro Thr Pro Trp Gly Asp Leu Glu Val Tyr Gln
305                 310                 315                 320

Tyr Asn Gly Lys Tyr Thr Gln His Cys Ala Ala Val Asp Ser Ser Glu
                325                 330                 335

Cys Ile Glu Val Pro Asp Ile Arg Pro Glu Phe Asn Pro Trp Gln Tyr
            340                 345                 350

Asp Asn Leu Asp Ala Glu
            355

<210> SEQ ID NO 31
<211> LENGTH: 300
<212> TYPE: PRT
<213> ORGANISM: Glycine max

<400> SEQUENCE: 31

Met Cys Asn Asn Gly Gln Ser Pro Leu Asp Arg Phe Ile Ser Val Val
1               5                   10                  15

Ala Trp Cys Ile Ser Thr Thr Arg Pro Val Thr Phe Gly Val Ala Pro
                20                  25                  30

Tyr Asn Pro Ile Leu Gly Glu Thr His His Val Ser Arg Gly Asn Leu
            35                  40                  45

Asn Val Leu Leu Glu Gln Ile Ser His His Pro Pro Val Thr Ala Leu
    50                  55                  60

His Ala Thr Asp Glu Lys Glu Asn Ile Glu Met Leu Trp Cys Gln Arg
65                  70                  75                  80

Pro Asp Pro Lys Phe Asn Gly Thr Ser Val Glu Ala Lys Val His Gly
                85                  90                  95

Ile Arg Gln Leu Lys Leu Leu Asn His Gly Glu Thr Tyr Glu Met Asn
            100                 105                 110

Cys Pro Arg Leu Leu Leu Arg Ile Leu Pro Val Pro Gly Ala Asp Trp
        115                 120                 125

Ala Gly Thr Val Asn Ile Arg Cys Leu Glu Thr Gly Leu Val Ala Glu
    130                 135                 140

Leu Ser Tyr Arg Ser Ser Ser Phe Leu Gly Ile Gly Asn His Arg
145                 150                 155                 160

Val Ile Lys Gly Lys Ile Leu Asp Ser Ser Leu Lys Val Leu Tyr
                165                 170                 175

Glu Val Asp Gly His Trp Asp Arg Thr Val Lys Val Lys Asp Thr Asn
            180                 185                 190

Asn Gly Lys Val Arg Val Ile Tyr Asp Ala Lys Glu Val Met Ser Gly
        195                 200                 205

Leu Glu Thr Pro Ile Leu Lys Asp Ile Glu Gly Val Trp Gln Thr Glu
    210                 215                 220
```

```
Ser Ala His Val Trp Gly Glu Leu Asn Gln Ala Ile Val Ser Lys Asp
225                 230                 235                 240

Trp Glu Lys Ala Arg Glu Ala Lys Leu Lys Val Glu Arg Gln Arg
            245                 250                 255

Glu Leu Val Arg Glu Arg Ser Lys Gly Glu Thr Trp Ile Ser Lys
                260                 265                 270

His Phe Val Val Ser Asn Asn Lys Glu Gly Trp Gln Cys Ser Pro Ile
            275                 280                 285

His Lys Ser Val Pro Ala Ala Pro Ile Thr Ala Leu
    290                 295                 300

<210> SEQ ID NO 32
<211> LENGTH: 355
<212> TYPE: PRT
<213> ORGANISM: Glycine max

<400> SEQUENCE: 32

Met Ala Glu Leu Met Glu Tyr Ser Tyr Leu Leu Asp Met Ala Asp Lys
1               5                   10                  15

Thr Glu Asp Pro Tyr Met Arg Leu Val Tyr Ala Ser Ser Phe Phe Ile
            20                  25                  30

Ser Val Tyr Tyr Ala Tyr Gln Arg Thr Trp Lys Pro Phe Asn Pro Ile
        35                  40                  45

Leu Gly Glu Thr Tyr Glu Met Val Asn His Gly Ile Thr Phe Ile
50                  55                  60

Ser Glu Gln Val Ser His Pro Pro Met Ser Ala Gly His Ala Glu
65              70                  75                  80

Thr Glu His Phe Thr Tyr Asp Val Thr Ser Lys Leu Lys Thr Lys Phe
            85                  90                  95

Leu Gly Asn Ser Val Asp Val Tyr Pro Val Gly Arg Thr Arg Val Thr
            100                 105                 110

Leu Lys Arg Asp Gly Val Val Leu Asp Leu Val Pro Pro Thr Lys
        115                 120                 125

Val Ser Asn Leu Ile Phe Gly Arg Thr Trp Ile Asp Ser Pro Gly Glu
130                 135                 140

Met Ile Leu Thr Asn Leu Thr Thr Gly Asp Lys Val Val Leu Tyr Phe
145                 150                 155                 160

Gln Pro Cys Gly Trp Phe Gly Ala Gly Arg Tyr Glu Val Asp Gly Tyr
            165                 170                 175

Val Tyr Asn Ser Ala Asp Glu Pro Lys Ile Leu Met Thr Gly Lys Trp
            180                 185                 190

Asn Glu Ala Met Asn Tyr Gln Val Cys Asp Ser Glu Gly Glu Pro Leu
            195                 200                 205

Pro Gly Thr Glu Leu Lys Glu Ile Trp Arg Val Ala Asp Thr Pro Lys
    210                 215                 220

Lys Asp Lys Phe Gln Tyr Thr His Phe Ala His Lys Ile Asn Ser Phe
225                 230                 235                 240

Asp Thr Ala Pro Lys Leu Leu Ala Ser Asp Ser Arg Leu Arg Pro
            245                 250                 255

Asp Arg Met Ala Leu Glu Lys Gly Asp Leu Ser Thr Ser Gly Tyr Glu
            260                 265                 270

Lys Ser Ser Leu Glu Glu Arg Gln Arg Ala Glu Lys Arg Asn Arg Glu
        275                 280                 285

Ala Lys Gly His Lys Phe Thr Pro Arg Trp Phe Asp Leu Thr Asp Glu
```

```
            290                 295                 300
Val Thr Pro Thr Pro Trp Gly Asp Leu Glu Val Tyr Gln Tyr Asn Gly
305                 310                 315                 320

Lys Tyr Thr Gln His Cys Ala Ala Val Asp Ser Ser Glu Cys Ile Glu
                325                 330                 335

Val Pro Asp Ile Arg Pro Glu Phe Asn Pro Trp Gln Tyr Asp Asn Leu
            340                 345                 350

Asp Ala Glu
        355

<210> SEQ ID NO 33
<211> LENGTH: 414
<212> TYPE: PRT
<213> ORGANISM: Zea mays

<400> SEQUENCE: 33

Met Ala Thr Lys Glu Glu Ala Ser Ala Val Pro Ala Ala Ser Lys Thr
1               5                   10                  15

Ser Trp Ser Ser Phe Leu Lys Ser Ile Ala Ser Phe Asn Gly Asp Leu
                20                  25                  30

Ser Ser Leu Thr Ala Pro Pro Phe Ile Leu Ser Thr Thr Ser Leu Thr
            35                  40                  45

Glu Tyr Ser Ala Tyr Trp Cys Glu His Pro Ala Leu Phe Val Ala Pro
50                  55                  60

Ala Arg Glu Pro Asp Pro Ala Lys Arg Ala Leu Leu Val Leu Lys Trp
65                  70                  75                  80

Phe Leu Ser Thr Leu His Gln Gln Tyr Cys Ser Arg Ser Glu Lys Leu
                85                  90                  95

Gly Ser Glu Lys Lys Pro Leu Asn Pro Phe Leu Gly Glu Leu Phe Leu
            100                 105                 110

Gly Lys Trp Ile Glu Asp Glu Asp Val Gly Glu Thr Arg Leu Ile Ser
        115                 120                 125

Glu Gln Val Ser His His Pro Pro Ala Thr Ala Tyr Ser Ile Val Asn
130                 135                 140

Glu Lys His Gly Val Glu Leu Gln Gly Tyr Asn Ala Gln Lys Ala Ser
145                 150                 155                 160

Phe Ser Ser Thr Ile Gln Val Lys Gln Leu Gly His Ala Tyr Leu Ser
                165                 170                 175

Leu Thr Pro Pro Gly Lys Asp Ala Asn Asn Glu Asp Asp Arg Glu His
            180                 185                 190

Tyr Leu Ile Thr Leu Pro Asn Leu His Ile Glu Ser Leu Ile Tyr Gly
        195                 200                 205

Thr Pro Phe Val Glu Leu Glu Lys Ser Cys Lys Ile Ala Ser Ser Thr
210                 215                 220

Gly Tyr Ile Ser Lys Ile Asp Phe Ser Gly Lys Gly Trp Leu Ser Gly
225                 230                 235                 240

Lys Lys Asn Thr Phe Ser Ala Val Leu Tyr Lys Glu Ser Asp Gly Glu
                245                 250                 255

Lys Asn Pro Leu Tyr Thr Ala Asp Gly Gln Trp Ser Ser Phe Thr
            260                 265                 270

Ile Arg Asp Ala Arg Ala Lys Lys Asp Ile Glu Thr Phe Thr Ile Ser
        275                 280                 285

Asn Leu Lys Thr Thr Pro Leu Thr Val Ala Pro Leu Asp Glu Gln Asp
290                 295                 300
```

```
Glu Trp Glu Thr Arg Arg Ala Trp Arg Asp Val Ala Ala Ile Glu
305                 310                 315                 320

Arg Gly Asp Met Glu Ala Thr Ser Asn Ala Lys Thr Lys Ile Glu Val
            325                 330                 335

Ala Gln Arg Glu Leu Arg Lys Lys Glu Lys Glu Gln Gly Glu Glu Trp
        340                 345                 350

Glu Arg Arg Phe Phe Lys Arg Val Asn Glu Lys Asp Glu Pro Thr Phe
            355                 360                 365

Met Arg Leu Ala Ala Met Leu Asp Leu Thr Gln Gly Ile Glu Ser Asp
    370                 375                 380

Arg Thr Gly Gly Val Trp Arg Phe Asp Pro Ser Arg Ala Val Asp Ala
385                 390                 395                 400

Asn Pro Pro Tyr His Lys Val Gly Gly Glu Gly Leu Gly Leu
                405                 410
```

<210> SEQ ID NO 34
<211> LENGTH: 434
<212> TYPE: PRT
<213> ORGANISM: Saccharomyces cerevisiae

<400> SEQUENCE: 34

```
Met Ser Gln His Ala Ser Ser Ser Trp Thr Ser Phe Leu Lys Ser
1               5                   10                  15

Ile Ser Ser Phe Asn Gly Asp Leu Ser Ser Leu Ser Ala Pro Pro Phe
            20                  25                  30

Ile Leu Ser Pro Thr Ser Leu Thr Glu Phe Ser Gln Tyr Trp Ala Glu
        35                  40                  45

His Pro Ala Leu Phe Leu Glu Pro Ser Leu Ile Asp Gly Glu Asn Tyr
    50                  55                  60

Lys Asp His Cys Pro Phe Asp Pro Asn Val Glu Ser Lys Glu Val Ala
65                  70                  75                  80

Gln Met Leu Ala Val Val Arg Trp Phe Ile Ser Thr Leu Arg Ser Gln
                85                  90                  95

Tyr Cys Ser Arg Ser Glu Ser Met Gly Ser Glu Lys Lys Pro Leu Asn
            100                 105                 110

Pro Phe Leu Gly Glu Val Phe Val Gly Lys Trp Lys Asn Asp Glu His
        115                 120                 125

Pro Glu Phe Gly Glu Thr Val Leu Leu Ser Glu Gln Val Ser His His
    130                 135                 140

Pro Pro Met Thr Ala Phe Ser Ile Phe Asn Glu Lys Asn Asp Val Ser
145                 150                 155                 160

Val Gln Gly Tyr Asn Gln Ile Lys Thr Gly Phe Thr Lys Thr Leu Thr
                165                 170                 175

Leu Thr Val Lys Pro Tyr Gly His Val Ile Leu Lys Ile Lys Asp Glu
            180                 185                 190

Thr Tyr Leu Ile Thr Thr Pro Pro Leu His Ile Glu Gly Ile Leu Val
        195                 200                 205

Ala Ser Pro Phe Val Glu Leu Gly Gly Arg Ser Phe Ile Gln Ser Ser
    210                 215                 220

Asn Gly Met Leu Cys Val Ile Glu Phe Ser Gly Arg Gly Tyr Phe Thr
225                 230                 235                 240

Gly Lys Lys Asn Ser Phe Lys Ala Arg Ile Tyr Arg Ser Pro Gln Glu
                245                 250                 255

His Ser His Lys Glu Asn Ala Leu Tyr Leu Ile Ser Gly Gln Trp Ser
            260                 265                 270
```

```
Gly Val Ser Thr Ile Ile Lys Lys Asp Ser Gln Val Ser His Gln Phe
        275                 280                 285

Tyr Asp Ser Ser Glu Thr Pro Thr Glu His Leu Leu Val Lys Pro Ile
    290                 295                 300

Glu Glu Gln His Pro Leu Glu Ser Arg Arg Ala Trp Lys Asp Val Ala
305                 310                 315                 320

Glu Ala Ile Arg Gln Gly Asn Ile Ser Met Ile Lys Lys Thr Lys Glu
                325                 330                 335

Glu Leu Glu Asn Lys Gln Arg Ala Leu Arg Glu Gln Glu Arg Val Lys
                340                 345                 350

Gly Val Glu Trp Gln Arg Arg Trp Phe Lys Gln Val Asp Tyr Met Asn
        355                 360                 365

Glu Asn Thr Ser Asn Asp Val Glu Lys Ala Ser Glu Asp Ala Phe
    370                 375                 380

Arg Lys Leu Ala Ser Lys Leu Gln Leu Ser Val Lys Asn Val Pro Ser
385                 390                 395                 400

Gly Thr Leu Ile Gly Gly Lys Asp Asp Lys Lys Asp Val Ser Thr Ala
                405                 410                 415

Leu His Trp Arg Phe Asp Lys Asn Leu Trp Met Arg Glu Asn Glu Ile
                420                 425                 430

Thr Ile
```